US011080541B2

(12) United States Patent
Ranalletta et al.

(10) Patent No.: US 11,080,541 B2
(45) Date of Patent: Aug. 3, 2021

(54) WORK STATION FOR MEDICAL DOSE PREPARATION SYSTEM

(71) Applicant: BAXTER CORPORATION ENGLEWOOD, Englewood, CO (US)

(72) Inventors: Joseph V. Ranalletta, Englewood, CO (US); Wesley J. Weber, Golden, CO (US)

(73) Assignee: Baxter Corporation Englewood, Englewood, CO (US)

( * ) Notice: Subject to any disclaimer, the term of this patent is extended or adjusted under 35 U.S.C. 154(b) by 0 days.

(21) Appl. No.: 16/869,922

(22) Filed: May 8, 2020

(65) Prior Publication Data

US 2020/0261318 A1   Aug. 20, 2020

Related U.S. Application Data

(63) Continuation of application No. 16/027,805, filed on Jul. 5, 2018, now Pat. No. 10,646,405, which is a
(Continued)

(51) Int. Cl.
*G06K 9/20* (2006.01)
*G06Q 10/06* (2012.01)
(Continued)

(52) U.S. Cl.
CPC .......... *G06K 9/2018* (2013.01); *A47B 13/003* (2013.01); *A47B 13/10* (2013.01);
(Continued)

(58) Field of Classification Search
CPC ........ A61J 3/00; A61J 7/0076; A61J 2200/74; A47B 37/00; A47B 2037/005;
(Continued)

(56) References Cited

U.S. PATENT DOCUMENTS 6,610,973 B1 * 8/2003 Davis, III ................. A61J 7/02
250/222.1
7,028,723 B1 * 4/2006 Alouani ................. B65B 5/101
141/83
(Continued)

FOREIGN PATENT DOCUMENTS

JP          H 07204253 A      8/1995
JP          2004340770 A     12/2004
(Continued)

OTHER PUBLICATIONS

Japanese Office Action Reason for Refusal dated Jun. 2, 2020 in correspondence Japanese Patent Application No. 2019-088657.

*Primary Examiner* — Allen C Wong
(74) *Attorney, Agent, or Firm* — K&L Gates LLP

(57) ABSTRACT

Embodiments of work stations for use in medical dose preparation management system. A work station may include a camera stand. The camera stand may include a housing enclosing a camera and one or more light sources therein. As such, the camera and light sources may be directed at a medical dose preparation staging region to capture medical dose preparation images of the medical dose preparation staging region. The camera stand may include an adjustable support positionable in a plurality of positions to dispose the camera and light source relative to the medical dose preparation staging region. A base with a removable tray may be provided that include medical receptacle engagement features. The work stations may facilitate improved image quality, efficiency of work flows carried out at the work station, and administrative tasks such as cleaning.

20 Claims, 15 Drawing Sheets

Related U.S. Application Data continuation of application No. 15/193,494, filed on Jun. 27, 2016, now Pat. No. 10,045,912, which is a continuation of application No. 14/438,559, filed as application No. PCT/US2013/032545 on Mar. 15, 2013, now Pat. No. 9,375,079.

(60) Provisional application No. 61/719,256, filed on Oct. 26, 2012.

(51) Int. Cl.

| | | |
|---|---|---|
| *G16H 40/63* | (2018.01) | |
| *A61J 3/00* | (2006.01) | |
| *A47B 37/00* | (2006.01) | |
| *F21V 9/14* | (2006.01) | |
| *H04N 7/18* | (2006.01) | |
| *A47B 13/00* | (2006.01) | |
| *A47B 13/10* | (2006.01) | |
| *G01G 19/414* | (2006.01) | |
| *A61J 7/00* | (2006.01) | |
| *H04N 5/225* | (2006.01) | |
| *H04N 5/232* | (2006.01) | |
| *G16H 20/13* | (2018.01) | |
| *G16H 20/10* | (2018.01) | |
| *F21Y 115/10* | (2016.01) | |

(52) U.S. Cl.
CPC ............... *A47B 37/00* (2013.01); *A61J 3/00* (2013.01); *A61J 7/0076* (2013.01); *F21V 9/14* (2013.01); *G01G 19/414* (2013.01); *G06Q 10/06395* (2013.01); *G16H 20/10* (2018.01); *G16H 20/13* (2018.01); *G16H 40/63* (2018.01); *H04N 5/2252* (2013.01); *H04N 5/2256* (2013.01); *H04N 5/23216* (2013.01); *H04N 7/18* (2013.01); *H04N 7/183* (2013.01); *A47B 2037/005* (2013.01); *A61J 2200/74* (2013.01); *F21Y 2115/10* (2016.08)

(58) Field of Classification Search
CPC .... A47B 13/003; A47B 13/10; G06K 9/2018; G16H 40/63; G16H 20/13; G16H 20/10; G01G 19/414; G06Q 10/06395; F21V 9/14; F21Y 2115/10; H04N 7/18; H04N 7/183; H04N 5/2252; H04N 5/2256; H04N 5/23216
USPC ......................................................... 348/143
See application file for complete search history.

(56) References Cited

U.S. PATENT DOCUMENTS

| | | | |
|---|---|---|---|
| 2004/0105271 A1* | 6/2004 | Chen | F21V 21/28 362/402 |
| 2004/0181268 A1* | 9/2004 | Anderer | F21V 21/22 607/90 |
| 2007/0047980 A1 | 3/2007 | Limer et al. | |
| 2008/0214333 A1* | 9/2008 | Peery | A63B 63/083 473/483 |
| 2009/0157537 A1* | 6/2009 | Miller | G06Q 10/109 705/32 |
| 2009/0188937 A1* | 7/2009 | Kim | G07F 11/62 221/312 B |
| 2009/0189988 A1* | 7/2009 | Jia | G05B 19/042 348/211.4 |
| 2011/0090350 A1* | 4/2011 | Oomori | H04N 5/2252 348/207.99 |

FOREIGN PATENT DOCUMENTS

| | | |
|---|---|---|
| JP | 2010056619 A | 3/2010 |
| JP | 2012078265 A | 4/2012 |

* cited by examiner

WORK STATION FOR MEDICAL DOSE PREPARATION SYSTEM

RELATED APPLICATIONS

This application is a continuation of U.S. patent application Ser. No. 16/027,805, having a filing date of Jul. 5, 2018, now U.S. Pat. No. 10,646,405, entitled "WORK STATION FOR MEDICAL DOSE PREPARATION SYSTEM", which is a continuation of U.S. patent application Ser. No. 15/193,494, having a filing date of Jun. 27, 2016, now U.S. Pat. No. 10,045,912, entitled "WORK STATION FOR MEDICAL DOSE PREPARATION SYSTEM", which is a continuation of U.S. patent application Ser. No. 14/438,559, now U.S. Pat. No. 9,375,079, having a 371(c) filing date of Apr. 24, 2015, entitled "WORK STATION FOR MEDICAL DOSE PREPARATION SYSTEM," which is a U.S. National Stage of International Patent Application No. PCT/US2013/032545, filed Mar. 15, 2013, entitled "IMPROVED WORK STATION FOR MEDICAL DOSE PREPARATION SYSTEM," which claims the benefit of and priority to U.S. Provisional Patent Application No. 61/719,256 filed Oct. 26, 2012, entitled "WORK STATION FOR MEDICAL DOSE PREPARATION SYSTEM," all of which foregoing patent applications are incorporated herein by reference in their entirety.

BACKGROUND OF THE INVENTION

Many care providers have a pharmacy that prepares medical doses for administration to patients that are treated by the care provider. In this regard, the pharmacies may employ a formulary to prepare medications in order to fulfill medical dose orders that are ordered by care provider personnel (e.g., physicians) for administration to patients. Some medical doses to be prepared may include compounded sterile products (CSPs) that may be prepared in specially constructed and controlled environment (e.g., an "IV Room") in the pharmacy. The process of preparing medical doses may be carried out in accordance with local policy, governmental regulations, industry organizations (e.g., Chapter <797> of the United States Pharmacopoeia), or other applicable policies. For example, the preparation of medications may generally occur in a laminar airflow hood, isolator, or biological safety cabinet, by an operator (typically a pharmacy technician) who is tasked with preparing the medical doses. Once the medical doses are prepared, the medical doses may be required to be verified by a pharmacist prior to being dispensed from the pharmacy for administration to a patient.

In traditional pharmacy management techniques, medical dose orders may be provided to a printer that prints labels indicative of the medical dose order that are to be applied to finished doses once the doses are prepared. A pharmacy technician may be required to retrieve labels from a label printer and use those labels as work order travelers in the process of preparing each dose. Once the dose prepared, the technician may apply a label to the dose. The completed, labeled dose may be set aside for a pharmacist to check along with, for example, source ingredients, medicament receptacles used in the course of preparing the dose, and/or other material. In this regard, in order to check a dose, the pharmacist may be required to enter the clean room in which the doses are prepared and physically observe the materials associated with the dose order. As such, the checking of prepared doses may require the pharmacist to dress in protective clothing or equipment, which takes time and resources.

Furthermore, the only prompt a pharmacy may receive to prepare a medical dose order is the printing of the label. In this regard, if a label becomes lost or damaged, a dose may not be prepared. Additionally, prioritizing work also becomes difficult because the label stack at the label printer may be the only evidence of what doses have been ordered, prepared, and/or dispensed. As such, relying on physical labels alone to track doses may result in unprepared, lost, or duplicate doses. In some cases, pharmacies may produce duplicate labels as a matter of course such that the pharmacy must review each label against the other, already received labels, to determine if a label represents a new dose order that needs to be prepared. This practice may lead to increased administrative overhead in the pharmacy that add operational costs and reduce pharmacy efficiency.

Furthermore, while instructions for preparation of a drug may be recorded in official FDA-approved literature for the drug, pharmacy technicians may not reliably consult the literature when preparing doses. Rather, pharmacy technicians may memorize the steps needed for the most common drugs, and then generalize those steps to other drugs to be prepared without verifying the protocols associated with a particular drug. In this regard, if the dose order includes special instructions that a pharmacy technician does not recognize, references regarding the proper techniques may not be present or may not be consulted. Accordingly, dose orders including special instructions often must be prepared by more experienced technicians or at the direction of more experienced technicians. In either regard, the protocol used to prepare the dose may not conform to the FDA-approved literature for the drug being prepared.

Further still, in traditional pharmacy management techniques, the pharmacy technician may be responsible for creating records that are maintained in relation to doses that have been prepared and products from the formulary that were employed to make the dose. For example, a pharmacy technician may be tasked with transcribing information such as lot numbers, expiration dates, serial numbers, or the like. The manual creation of records requires labor intensive practices that may result in pharmacy inefficiencies, introduces the potential for errors in the records, and may result in virtually unsearchable paper records.

SUMMARY OF THE INVENTION

Embodiments of medical dose preparation management systems that may assist in management of medical doses are described herein. The embodiments described herein may include one or more work stations that are used to assist in preparation of a medical dose order. For example, the work stations may be used to provide guidance to a technician regarding the preparation of a medical dose order, and/or the work order stations may be used to capture, collect, or compile data (e.g., metadata) regarding the medical dose order. In this regard, metadata associated with the medical dose order may be stored in corresponding relation to the medical dose order such that the metadata may be accessible to a care provider before or after administration of the medical dose associated with the medical dose order to the patient. The metadata may include data regarding the prepared dose order, a component of the dose order, or the manner in which the prepared dose order or a component of the dose order was prepared. Accordingly, metadata captured, collected, or compiled at the work station may be used to organize, track, or otherwise manage medical dose orders. As such, examples of advantages facilitated by the medical dose preparation management system may include, among others, improved prioritization, organization, tracking, and records keeping for medical dose orders.

For example, the metadata regarding a dose order may include one or more medical dose preparation images related to components of a medical dose order, steps carried out during the preparation of a dose order, or a finished dose order. In this regard, the medical dose preparation images may be used to document or evidence the preparation of a medical dose order. It may be appreciated that the quality of the medical dose preparation images obtained by the medical dose preparation management system may be an important consideration in the medical dose preparation management system.

As such, it is presently recognized that the features and/or attributes of the work station may contribute to the accuracy, speed, and or quality at which the medical dose orders may be prepared by technicians at the work station while capturing, collecting, and/or compiling metadata (e.g., including medical dose preparation image data). As such, an objective of the present disclosure is to present work stations that facilitate efficient work flows to enable a technician to efficiently prepare medical dose orders while obtaining dose order metadata. Additionally, an objective of the present disclosure is to present work stations that facilitate the capture of high quality medical dose preparation images comprising dose order metadata. In this regard, the efficient capture of high quality dose order metadata during the preparation of a medical dose may contribute to patient safety, improve pharmacy efficiency, assist in pharmacy management, and/or provide other advantages as may be appreciated in the description presented herein. Furthermore, an objective of the present disclosure is to present work stations that may facilitate advantages related to administrative task performed at the work station such as work station cleaning.

Accordingly, a number of aspects are described herein that are related to a medical dose order management system. The various aspects discussed herein may be realized in isolation and/or in combination with one or more others of the aspects presented herein and thereby compose one or more additional aspects. In this application, the term aspect is used synonymous to the term embodiment. In other words, one or more features of one or more aspects and/or one or more features of one or more embodiments described in this application may be separated from the remaining features of the corresponding aspect and/or embodiment and combined with separated features of one or more aspects and/or embodiments to create new aspects and/or embodiments. In this regard, the aspects described herein may be used in the context of a work station of a medical dose management system as described above. In particular, the workstation may be adapted and suitable for the use in a system for medical dose preparation management. One aspect may relate to the use of a workstation for medical dose preparation management. Another aspect may relate to a medical dose management system and the workstation may be a component of the medical dose management system.

Accordingly, the work station may generally include an imaging device (e.g., digital camera) supported relative to a medication preparation staging region. The medical dose preparation staging region may be at least partially defined by a base having a length and a width. That is, the base may include a surface for supporting an object such as a medication receptacle used in the preparation of a medical dose order at the work station. The imaging device may have an imaging field encompassing at least a portion of the medication preparation staging region. The imaging device may be operable to capture digital image data (e.g., still digital images and/or video data stream) of the medical dose preparation staging region (e.g., including medication receptacles used in the medical dose order or prepared by the work station).

In this respect, one aspect may include an imaging device that is located at least partially within a housing. In turn, the imaging field of the imaging device may extend through an opening of the housing. Additionally, a transparent shield may be disposed between the imaging device and the medication preparation staging region. In particular, the transparent shield may cover at least a portion of the imaging device (e.g., corresponding to at least a lens of the imaging device). The transparent shield may extend across at least a portion of or substantially all of the opening through which the imaging field of the imaging device extends.

In the latter regard, the transparent shield and the housing may define an enclosed volume. As such, the transparent shield and the housing may define a continuous outer surface disposed about the enclosed volume. Thus, the imaging device may be disposed within the enclosed volume. As a result, the imaging device may be shielded from an environment external to the enclosed volume (e.g., the camera may be isolated from spills or other potential contact with liquids or hazardous substances such as may occur during dose preparation or during the cleaning of the work station).

In another aspect, an imaging device may be provided having at least one fixed optical setting. In an embodiment, the fixed optical setting may be preset (e.g., during the manufacture of the work station). The fixed optical setting may result in a depth of field that encompasses substantially the entire medical dose preparation staging region (e.g., such that an image of an object in the medical dose preparation staging region is disposed within the depth of field). In various embodiments, the at least one fixed optical setting may correspond to at least one of an aperture setting, a focus setting, a magnification setting, and/or other appropriate optical setting.

In another aspect, at least one light source (e.g., one or more LEDs) may be disposed in the housing. As such, the light source(s) may be operable to emit light from the housing in a direction toward the medication preparation staging region. As such, the light source may also be disposed in the enclosed volume such that the light source is also shielded from an environment external to the enclosed volume.

In still another aspect, light polarization filters may be employed in conjunction with a light source and an imaging device of the work station (e.g., to reduce glare in a medical dose preparation image captured by the imaging device). For example, the work station may include a first polarization filter disposed between the imaging device and the medication preparation staging region and a second polarization filter disposed between the light source and the medication preparation staging region. In an application, at least a portion of a transparent shield (e.g., as discussed above) may comprise at least one of the first or second polarization filters. In an embodiment the transparent shield may comprise both, the first and the second polarization filters. In an embodiment, the first polarization filter and the second polarization filter may collectively cover at least a portion of the opening of the housing. The first polarization filter and the second polarization filter may be disposed in non-overlapping relation, and the first polarization filter and the second polarization filter may have perpendicular polarization orientations. Accordingly, the polarization filters may work in conjunction to reduce glare from objects in the medication dose preparation staging region.

In an embodiment, the imaging device may be disposed in a central region of the housing opening and a peripheral region may extend about the central region. A plurality of light sources may be disposed in the peripheral region (e.g., spaced about the central region). In this regard, the first polarization filter may cover a portion of the opening corresponding to the lens of the camera and the second polarization filter may cover a portion of the opening corresponding to the light source(s).

In an embodiment, the peripheral region may extend in at least a first direction corresponding to the width of the base. The peripheral region may also extend in at least a second direction corresponding to one of the length of the base or a height of the medication dose preparation staging region extending from the base. For example, as described in greater detail below, the imaging device may be disposed in a plurality of positions relative to the medical dose preparation imaging device. Accordingly, depending upon the orientation of the imaging device, the peripheral region may extend in a direction corresponding to the length of the base and when in a second position, the peripheral region may extend in a direction corresponding to the height of the medical dose preparation staging region (e.g., extending normal to the base).

In this regard, a support member may extend between the base and the housing for supportably disposing the imaging device relative to the base (e.g., between a plurality of different positions of the imaging device relative to the base). That is, the support member may be selectively positionable in at least a first position and a second position relative to the medication preparation staging region of the base. The support member may be moveable between the first position and the second position. Additionally or alternatively, the support member may be selectively positionable in a plurality of different positions relative to the medication preparation staging region.

In an embodiment, the support member may include a first portion attached to the base and a second portion attached to the imaging device. The second portion may be moveable relative to the first portion between the first position and the second position. For instance, the first portion may be hingedly connected to the second portion. Accordingly, the first portion and the second portion may be pivotally disposable between the first position and the second position. In an embodiment, movement between the first position and the second position may be dampened.

When the support member is in the first position, the imaging field of the imaging device may extend between the imaging device and the base to encompass at least a portion of the medical dose preparation staging region. When the support member is in a second position, the imaging field may extend in a direction parallel to a support surface of the base to encompass at least a portion of the medical dose preparation staging region.

In one embodiment, the support member may extend from the base adjacent to an edge of the base extending along the width. The work station may be disposed in a laminar flow hood or the like. Accordingly, a flow of air from the laminar flow hood may be parallel to a direction corresponding to the width of the base. That is, the support may be positioned relative to the base so as not to obstruct the laminar flow of air across the base (e.g., substantially the entire base may be exposed to laminar air flow).

Furthermore, it is recognized that elimination and/or reduction of the number of wires, cables, and the like from the work station may be advantageous. For example, the reduction of wires and/or cables may provide fewer structures and surfaces that require cleaning. Furthermore, in the case where a containment structure such as a laminar airflow hood, isolator, or biological safety cabinet is used, the routing of cables to an exterior environment of the containment structure may present difficulties in maintaining an appropriate containment level of the containment structure. As such, the reduction and/or elimination of wires, cables, and the like at the work station may improve the ability to clean the work station and may assist in maintaining a level of containment of a containment structure employed at the work station.

In this regard, in an aspect, an umbilical may be provided that is at least partially disposed within a support member (e.g., to reduce the number of cables, wires, or the like in the work station). The umbilical may include at least one of a signal communication member and a power communication member. That is, the umbilical may consolidate a number of conductive members into a single cable to reduce the number of cables that need to be provided. The umbilical may be in operative communication with a processor.

In another embodiment, wireless technology may be incorporated at the work station (e.g., to completely eliminate the need for wires and the like). That is, technology may be incorporated into the work station to wirelessly communicate signals between the various components and the processor. For example, image data, lighting control data, scale information, or other communication between the devices of the work station and a processor may be facilitated by way of wireless communication. Additionally, a battery may be provided with the camera stand to facilitate wireless operation. For example, the battery may be replaceable or rechargeable to facilitate continued wireless operation.

In an application, the base of the work station may be supportably engageable with a surface with one or more suction cups. In this regard, the camera stand may be securely retained on a surface. Furthermore, the suction cups may provide some measure of vibration isolation from an exterior environment.

In another aspect, a support platform may be provided that is removably disposable relative to the base. The removal of the support platform may facilitate cleaning of the support platform. The support platform may at least partially define the medication preparation staging region. The support platform may be made of a UV resistant material to withstand discoloration or deterioration of the support platform.

In an aspect, a support surface of the support platform may define a plurality of medication receptacle engagement features. Accordingly, the support platform may include a reference plane corresponding to a surface of the support surface. In this regard, the support surface may include at least one groove defined in the support surface that may extend from the reference plane by a first depth. Additionally, the support surface may include at least one channel defined in the support surface that may extend from the reference plane by a second depth. The groove and the channel may be operable to engage a medication receptacle disposed in the medication preparation staging region. In an embodiment, the first depth may be less than the second depth.

Also, in one implementation, the groove may include a first concave surface extending from the reference plane to the first depth. The channel may comprise a second concave surface extending from the reference plane to the second depth. The first concave surface may have a first radius of curvature greater than a second radius of curvature of the second concave surface. In an embodiment, the support surface may include a plurality of grooves and/or a plurality of channels. At least one of said plurality of grooves may be disposed perpendicular to at least one of the channels. Furthermore, at least one of the plurality of grooves may extend in a first direction of the base corresponding to a width of the support surface. For example, at least one groove may extend across substantially all of the support surface in a first direction corresponding to the width of the support surface. Also, at least one of the plurality of channels may extend in a second direction of the base corresponding to the length of the support surface. For example, at least one channel may extend across substantially all of the support surface in a second direction corresponding to a length of the support surface.

Still another aspect may include a mechanism for alerting a user to the fact that a medical dose preparation image has been captured. For example, a user control device (e.g., a foot switch) may be provided that is in operative communication with the processor to initiate a capture of a medical dose preparation image from the image data obtained by the image device in response to a user input received at the user control device. In other words, the user control device may be operable to and/or adapted to receive a user input for receiving a user input to initiate capture of a medical dose preparation image from a video data stream output by the imaging device. Alternatively or additionally, other methods of triggering capture of a medical dose preparation image may be provided without limitation. In any regard, upon capture of a medical dose preparation image, an intensity of a light source may be automatically modified from a default intensity of light emitted to a modified intensity of light. In other words the light source may be operable and/or adapted such that an intensity of the at least one light source is automatically modified from a default intensity of light emitted to a modified intensity of light emitted. The change in light intensity may occur at a first predetermined period after the capture of the medical dose preparation image. Furthermore, the light source may be automatically returned from the modified intensity of light to the default intensity of light at a second predetermined period after the first predetermined period. In other words, the light source may operable to and/or adapted to be automatically returned from the modified intensity of light to the default intensity of light at a second predetermined period after the first predetermined period. The light source may be automatically returnable from the modified intensity of light to the default intensity of light. In this regard, the light source may be controlled to "blink" or "flicker" to indicate to a user that the image has been captured so that the user may proceed in the workflow.

In an embodiment, a scale may be provided that is in operative communication with the processor. The scale may be operable to output a weight corresponding to a medication receptacle that is supportably disposed in the medication preparation staging region. In this regard, the scale may be provided in corresponding relation to the base (e.g., disposed relative to the base and/or integrated with the base).

For example, the scale may be generally used to perform a gravimetric analysis of an item disposed in the medical dose preparation staging region. For example, upon capture of a medical dose preparation image, the weight of the medication receptacle may be recorded by the processor from the scale at substantially the same time that the medical dose preparation image is captured. In other words, the processor may be operable to and/or adapted to—upon receipt of a user input—record the weight from the scale at substantially the same time that the medical dose preparation image is captured. In this regard, the work station may also include a memory in operative communication with the processor for storing the weight and the medical dose preparation image. For example, the weight and the medical dose preparation image may be associatively stored in the memory. As such, the processor may be operable to compare the measured weight of the medication receptacle to an anticipated weight of the medication receptacle (e.g., provided in metadata of the order). In this regard, the processor may be operable to calculate a deviation of the measured weight to the anticipated weight. The deviation may be associatively stored in the memory with the weight, the medical dose preparation image, and/or the dose order. Furthermore, the deviation may be compared to a threshold deviation value. Accordingly, when the deviation exceeds a threshold deviation, an alert may be provided to a user. In this aspect, the base, the imaging device, and the scale may be interconnected for movement as a single unit. Moreover, the processor may be operable to and/or adapted to compare the deviation to the threshold deviation, and provide the alert to the user.

Another aspect may relate to a method comprising the steps of outputting of a video data stream of the imaging field, receiving the video data stream of the imaging field, initiating a capture of a medical dose preparation image from the video data stream in response to a user input received at a user control device, and outputting a weight corresponding to a medication receptacle that is supportably disposed in a medication preparation staging region. The method may further provide for upon receipt of the user input, recording of the weight at substantially the same time as the capture of the medical dose preparation image.

Numerous additional features and advantages of the present invention will become apparent to those skilled in the art upon consideration of the embodiment descriptions provided hereinbelow.

DETAILED DESCRIPTION

Figure 1:
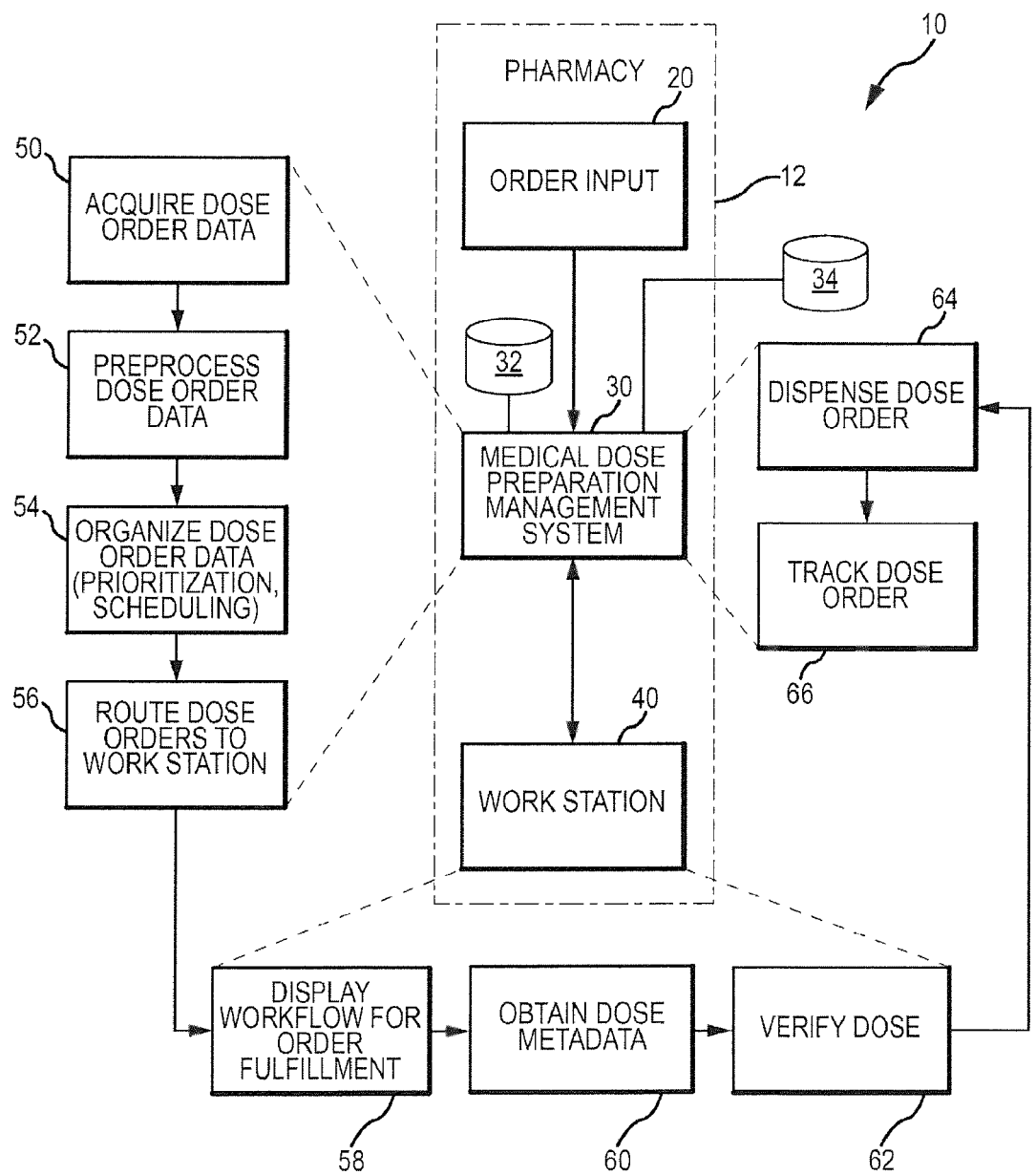
FIG. 1 is a schematic and flow chart depicting an embodiment of a medical dose preparation management system and an embodiment of the operation thereof.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

FIG. 1 shows an embodiment of a system 10 that may be used at a care provider pharmacy 12 to assist in the preparation and/or management of medical doses. The system 10 may include a dose order input 20 to receive medical dose orders. The dose order input 20 may be utilized by care provider personnel (e.g., physicians, nurses, etc.) to order medical doses.

The medical dose orders received at the dose order input 20 may be specific to patients or may be orders that are not associated with a patient at the time of ordering. In this regard, the medical dose order may correspond to a contained medication unit that may comprise one of the following:

a patient specific unit comprising a medication unit designated for administration to a specific patient;

a non-patient specific unit comprising a medication unit to be subsequently designated for administration to a specific patient; or, a medication component source unit to be used in the preparation of a patient specific unit or a non-patient specific unit (e.g., that will be designated for administration to a specific patient after preparation).

Examples of contained medication units that may correspond to medication dose orders include:

compounded sterile products;

injectable medications;

chemotherapy preparations; or nutritional supplements requiring administration by a patient care provider (e.g., sterile injectable nutritional supplements).

In the latter regard, nutritional supplements may include total parenteral nutrition (TPN) or components of TPN. Furthermore, nutritional supplements may include partial nutritional supplements. The nutritional supplements may include a pre-mix bag, base and additive components separately or in combination, or other forms of nutritional supplements or components thereof. The nutritional supplements may be for administration via intravenous injections, in an edible form, or for use with a feeding tube or the like.

In any regard, the medical dose may include one or more portions of information that may be used to assist in preparation of the mediation dose, may be associated with the administration of the dose order to a patient, or may otherwise relate to the dose order. For example, the dose order may include information corresponding to:

a medication identity;

a medication amount;

a medication concentration;

information associated with a patient to whom the medication unit associated with the medication dose order is to be administered;

scheduling information (e.g., an administration time) for the medication unit associated with medication dose order; or other appropriate information regarding the medication unit associated with the medication dose order.

In any regard, the medical dose orders may be communicated to a medical dose preparation management system 30. The medical dose preparation management system 30 may be operable to acquire 50 dose order data from the dose order information received from the order processor 20. The medical dose preparation management system 30 may also preprocess 52 dose order data. The preprocessing 52 may include, for example, generating a digital dose order record that is maintained by the medical dose preparation management system 30. The digital dose order record may be automatically populated with data that may be obtained from the order such as, for example, any of the information described above in connection with the medical dose order. In this regard, information may be parsed, scraped, or otherwise obtained from the medication dose order received at the order input 20. Specifically, in an embodiment, the medical dose preparation management system 30 may be operable to scrape data addressed to a human readable output (e.g., a printer) from the order input 20 to populate the medical dose order record with data corresponding to the medical dose order.

In an embodiment, the medical dose preparation management system 30 may be in operative communication with a mediation dose order database 32. In this regard, the medication dose order database 32 may be located at the care provider facility (i.e., be on-site relative to the care provider hospital 12). The medical dose preparation management system 30 may additionally or alternatively be operable to communicate with a remote medication dose order database 34. In this regard, the medical dose preparation management system 30 may communicate with the remote medication dose order database 34 via a network or the like. In either regard, the medication dose order database 32 or 34 may be operable to store medication dose order records in the medication dose order database 32 and/or 34. In addition, the medication dose order database 32 or 34 may store dose order metadata in corresponding relation to respective ones of the stored medication dose orders. The medication dose order database 32 or 34 may store active dose orders (e.g., corresponding to dose orders that have been generated but not yet administered to the patient) or archived dose orders (e.g., corresponding to dose orders that have been administered to a patient). Redundant data may be stored at the on-site medical dose order database 32 and the off-site medical dose order database 34. For example, the off-site medical dose order database 34 may be a backup version of the on-site medical dose order database 32.

In any regard, medical dose order metadata may be stored in corresponding relation to a medication dose order. The medical dose order metadata may include, for example, the following types of data:

medication source data indicative of at least one of:
- a manufacturer of a component of the contained medication unit corresponding to the medication dose order,
- a lot number of a component of the contained medication unit corresponding to the medication dose order,
- an expiration date of a component of the contained medication unit corresponding to the medication dose order,
- a serial number of a component of the contained medication unit corresponding to the medication dose order, or
- a drug code indicative of the identity of a component of the contained medication unit corresponding to the medication dose order;

chain of custody data indicative of at least one of:
- a listing of entities in possession of a component of the contained medication unit corresponding to the medication dose order or the contained medication unit corresponding to the medication dose order,
- a listing of users that have taken an action with respect to the contained medication unit corresponding to the medication dose order, wherein the listing of users is correlated to specific actions taken by each user, or
- tracking information corresponding to physical movement of a component of the contained medication unit corresponding to the medication dose order or the contained medication unit corresponding to the medication dose order;

fulfillment data indicative of at least one of:
- image data corresponding with a component of the contained medication unit corresponding to the medication dose order or the contained medication unit corresponding to the medication dose order,
- scanned data obtained from a component of the contained medication unit corresponding to the medication dose order,
- analytic data regarding a component of the contained medication unit corresponding to the medication dose order or the contained medication unit corresponding to the medication dose order,
- pharmacist review data corresponding with at least one pharmacist review of a component of the contained medication unit corresponding to the medication dose order or the contained medication unit corresponding to the medication dose order,
- compliance data corresponding with best practices associated with a component of the contained medication unit corresponding to the medication dose order or the contained medication unit corresponding to the medication dose order,
- sterility assessment data corresponding to a component of the contained medication unit corresponding to the medication dose order or the contained medication unit corresponding to the medication dose order,
- a listing of actions corresponding to a component of the contained medication unit corresponding to the medication dose order or the contained medication unit corresponding to the medication dose order,
- time stamp data corresponding to actions corresponding to a component of the contained medication unit corresponding to the medication dose order or the contained medication unit corresponding to the medication dose order,
- a listing of life cycle events taken with respect a component of the contained medication unit corresponding to the medication dose order or the contained medication unit corresponding to the medication dose order
- weight data corresponding to a measured and/or anticipated weight of a component of the contained medication unit corresponding to the medication dose order or the contained medication unit corresponding to the medication dose order; or environmental data indicative of at least one of:
- a temperature to which a component of the contained medication unit corresponding to the medication dose order or the contained medication unit corresponding to the medication dose order has been exposed,
- a temperature to which and corresponding time period for which a component of the contained medication unit corresponding to the medication dose order or the contained medication unit corresponding to the medication dose order has been exposed,
- whether a component of the contained medication unit corresponding to the medication dose order or the contained medication unit corresponding to the medication dose order is refrigerated,
- whether a component of the contained medication unit corresponding to the medication dose order or the contained medication unit corresponding to the medication dose order is frozen,
- a temperature profile experienced by a component of the contained medication unit corresponding to the medication dose order or the contained medication unit corresponding to the medication dose order, or
- accelerometer data corresponding to forces experienced by a component of the contained medication unit corresponding to the medication dose order or the contained medication unit corresponding to the medication dose order.

As may be appreciated from the foregoing description of the medical dose order metadata, a medical dose order may inherit metadata from components used in the preparation of the medical dose order. In a simple example, a medical dose order may include a first component (e.g., a drug) to be mixed with a second component (e.g., a diluent). The first component may have one or more portions of metadata as described above that are associated with the first component. Additionally, the second component may have one or more portions of metadata as described above that are associated with the second component. Thus, a medical dose order that is prepared using the first component and the second component may inherit the metadata from each of the first component and second component. In this regard, a plurality of generations of metadata may be compiled and attributed for a given medical dose order. In an embodiment, metadata for any and all components used to prepare the dose order may be compiled and attributed for a given medical dose order. As such, metadata information for the medical dose order may include metadata originating with source components provided by a manufacturer of the components of a dose order.

The medical dose preparation management system 30 may also be operative to organize 54 dose orders. The organization 54 may include prioritization, scheduling, or other tasks associated with the organization or management of dose orders. The medical dose preparation management system 30 may also be operative to route 56 dose orders to an appropriate work station 40 for use in fulfillment of the dose order. In this regard, a plurality of work stations 40 may be provided in communication with the medical dose preparation management system 30. Different ones of the plurality of work stations 40 may each be suited for different operations related to medical dose order management. As such, depending on the nature of a medical dose, a particular type of work station 40 may be used to prepare the dose. The work station 40 may be on-site relative to the care provider hospital 12 as depicted in FIG. 1 or may be off-site. In this regard, the routing 56 may include communications over a network to a remote work station 40. Furthermore, the system 10 may include a combination of on-site work stations 40 as well as off-site work stations 40 to which dose orders may be routed 56.

In any regard, the medical dose preparation management system 30 may be in operative communication with one or more work stations 40. The routing 56 of dose orders may be at least partially based on one or more factors related to the dose order or the preparation of the dose order. For example, as stated above, the nature of the contained medication unit corresponding to the dose order (e.g., whether a dose order is a chemotherapy dose order, a parenteral dose order, or other specialized dose order) may factor into a determination regarding the routing 56 of the dose order. Additionally or alternatively, the capabilities of the various work stations 40 in relation to the manner in which the dose order is to be prepared may be considered. For example, some orders may require different levels of containment, hooding, or other precautions that may or may not be provided at each work station 40. In an embodiment, other parameters such as technician schedules, work station schedules, work station location, medication dose order scheduling information, or other information may be used alone or in combination to route 56 dose orders to a particular work station 40.

At the work station 40, a work flow corresponding to the preparation of the medical dose order may be displayed 58. In this regard, a work flow that is specific to the medical dose order currently being prepared at the work station 40 may be presented to a technician at the work station 40 to assist or provide guidance to the technician preparing the dose order. Accordingly, the technician may follow a sequence of steps to prepare the medical dose based on the work flow displayed 58 that relates to the dose order.

During and/or after the preparation of the dose order, the work station 40 may be used to assist in obtaining 60 dose order metadata related to the medical dose order. For example, the work station 40 may allow for recording of documentation regarding the preparation of the medical dose such as, for example, acquiring barcode scans of products, capturing medical dose preparation images of medical dose order receptacles during or after use in the preparation of the dose, or obtaining other information related to the preparation of the dose. In an embodiment, one or more of the types of data described above in relation to the medication dose metadata may be acquired in connection with the preparation of the medical dose order at the work station 40.

At least a portion of the dose metadata obtained 60 regarding the medication dose may be stored for viewing by appropriate personnel (e.g., a pharmacist). In this regard, the dose metadata may be utilized to verify 62 the prepared dose prior to the dose being dispensed from the pharmacy 12. In an embodiment, the metadata collected at the work station 40 may be made available to a pharmacist via a network. In this regard, a pharmacist tasked with verifying 62 a dose order may access the information and/or data remotely (e.g., in a location in the hospital but outside the IV room or even entirely remove from hospital premises via the network). The ability to remotely access the metadata may allow the pharmacist to avoid having to enter the IV room to verify 62 a dose order (i.e., thus avoid the potentially burdensome gowning procedures commonly associated with entering the controlled environment of an IV room). The verifying 62 may include inspection of medical dose preparation images, obtained information, or other data regarding the medical dose order by the pharmacist. For example, the pharmacist may verify the correct medication was prepared in the correct manner and/or in the correct amounts based on metadata gathered and stored during the preparation of the medical dose order. If the medication dose order is incorrect in any regard, the pharmacist may request the medication dose order be reworked or restarted.

Once the dose order has been prepared and verified 62, the medical dose preparation management system 30 may dispense 64 the dose order. When dispensing 64 the dose order, the dose order may be dispatched from the pharmacy 12 for administration to a patient by the care provider. For example, the dose may be administered at the care provider hospital 12 or an offsite location under the direction or supervision of the care provider.

The medical dose preparation management system 30 may also facilitate tracking 66 of the dose order to administration to the patient. The pharmacy work flow manager 30 may also retain records associated with each dose that may be stored or archived. For example, the records may be stored digitally in electronically indexed and searchable form. The records may include at least a portion and preferably all metadata regarding each dose.

Figure 2:
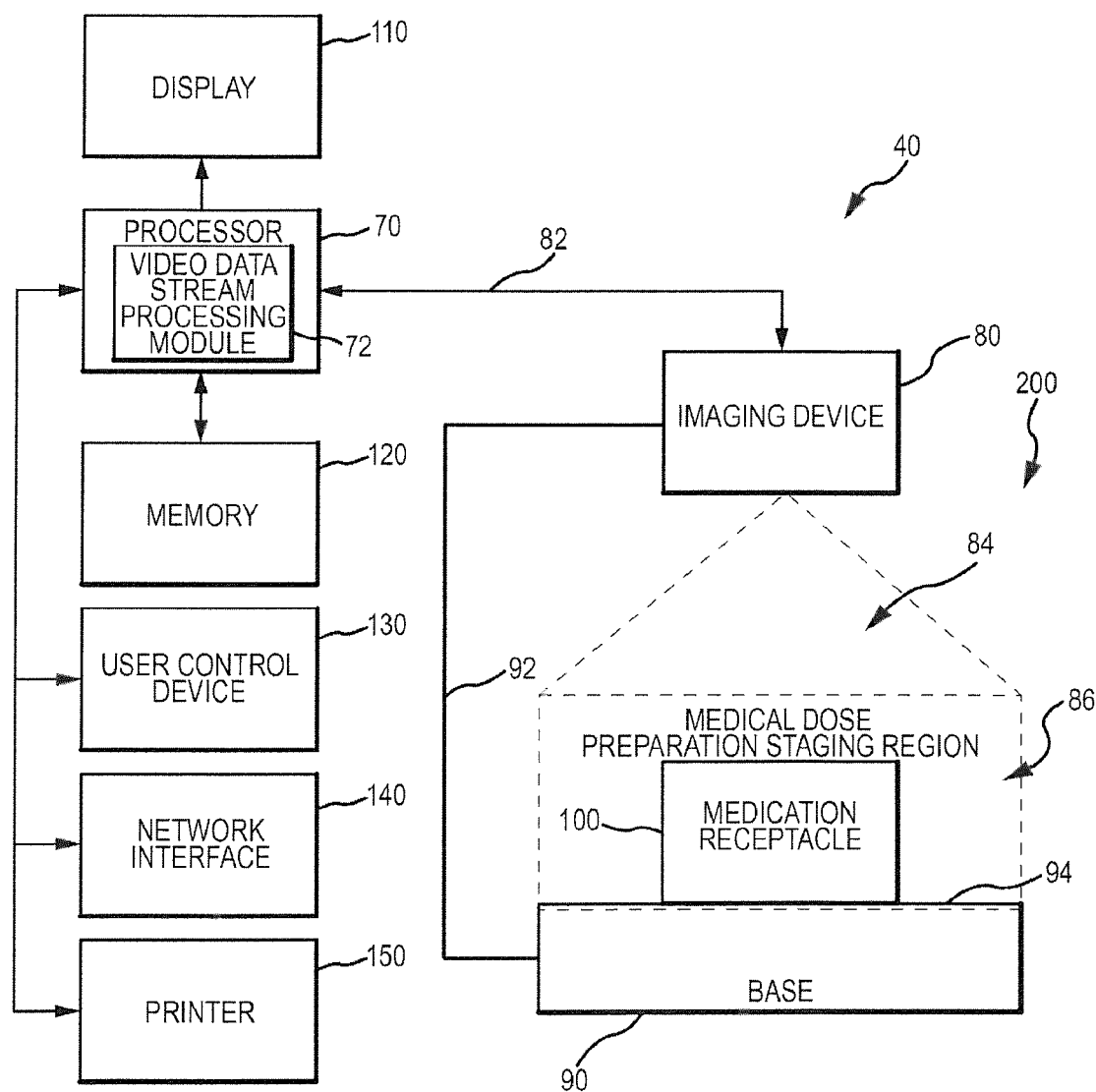
FIG. 2 is a schematic view of an embodiment of a work station for use in a medical dose preparation management system.

With further reference to FIG. 2, a schematic view depicting an embodiment of a work station 40 is shown. The work station 40 may include a processor 70 in operative communication with an imaging device 80. The imaging device 80 may be a digital camera operable to output digital image data. The digital image data may comprise still images and/or digital video. In this regard, the imaging device 80 may output a video data stream 82 that is received by the processor 70. In this regard, the processor 70 may include a video data stream processing module 72 for processing the video data stream 82 received at the processor 70 from imaging device 80. While the various components shown in FIG. 2 are shown in direct communication, the various components may also be in operative communication by way of a network interface or the like.

The imaging device 80 may include an imaging field 84. The imaging field 84 may encompass a medical dose preparation staging region 86. The imaging device 80 may be supportably mounted to a base 90. For example, a support 92 may extend from the base 90 to the imaging device 80 to support imaging device 80 relative to the base 80. In this regard, in an embodiment the medical dose preparation staging region 86 may include a support surface 94 of the base 90. The medical dose preparation staging region 86 may also include a volume above the surface 94 (e.g., extending from the surface in a direction normal to the surface and/or toward the imaging device 80). In any regard, the imaging field 84 of the imaging device 80 may encompass the medical dose preparation staging region 86 that may supportably receive a medication receptacle 100. In turn, the imaging device 80, support 92, and base 90 may collectively define a camera stand 200. As such, the camera stand 200 may be used at a work station 40 to support the imaging device 80 relative to the base 90 to obtain medical dose preparation image and/or other metadata during the preparation of the medical dose order.

The medication receptacle 100 supportable by the base 90 in the medical dose preparation staging region 86 may include any material, container, apparatus, or other object that is used in the preparation of a dose. For example, the medication receptacle 100 may be or include a source receptacle, a transference receptacle, or an administration receptacle. A source receptacle may store a medication product as stored in the pharmacy prior to compounding or dose preparation. In this regard, the source receptacle may be a receptacle as packaged by and received from a drug manufacturer. As such, the source receptacle may include information thereon relating to the medication. For example, the product name, concentration, amount, lot information, expiration information, a serial number, other manufacturing information or other information may be associated with the medication and/or may appear on the source receptacle. The medical dose preparation management system 30 may be operable to store metadata regarding the source receptacle including any of the foregoing portions of data that may appear on the source receptacle. In this regard, the source receptacle may be identifiable by the work station 40 (e.g., via the use of a machine readable indicium such as a bar code or the like).

Furthermore, the medical dose preparation management system 30 may be operable to attribute metadata from the source receptacle to the dose order in which the source receptacle is used as described above. The source receptacle metadata may even be attributed to or appended to the metadata for the medical dose order when the source receptacle comprises a pre-prepared medication that has been compounded at the pharmacy and disposed in the source receptacle for later use in the preparation of a dose. In this regard, the metadata for several generations of components used to prepare a medical dose order (e.g., originating from original source components received from a manufacturer such as a drug manufacturer) may be attributed to the medical dose order. As such, the medical dose order metadata may include information regarding all components used in the medical dose order including inherited metadata. The metadata for the various components may be retrieved upon identification of the receptacle 100 at the work station 40 (e.g., by way of scanning a machine readable indicium). In various embodiments, the source receptacle may include a vial, a syringe, a bottle, a bag, or other appropriate medication receptacle known in the art.

An administration receptacle may be any receptacle used during the administration of the medical dose to the patient. The administration receptacle may contain any medication, diluent, supplement, or any other material to be administered to the patient. In various embodiments, the administration receptacle may include a syringe, an IV bag, or other appropriate medication receptacle used in the administration of a substance to patient. An administration receptacle may also include metadata that is included in the metadata for the prepared medical dose order.

The transference receptacle may be used to transfer a substance from a source receptacle to the administration receptacle. For example, the transference receptacle may be a syringe or any other appropriate receptacle known in the art capable of transferring a substance from the source receptacle to the administration receptacle. A transference receptacle may also include metadata that is included in the metadata for the prepared medical dose order.

Returning to FIG. 2, the processor 70 may be in further operative communication with a display 110. In this regard, the video data stream 82 received from the imaging device 80 may be displayed on the display 110 in a manner that is perceivable by user. The video data stream 82 displayed on the display 110 may be processed by way of the video data stream processing module 72. For example, the video data stream processing module 72 may be operable to capture still images from the video data stream 82. The video data stream 82 may include a series of images displayed at a given frame rate. For example, the frame rate may be 5-10 frames/second.

Medical dose preparation images captured by the video data stream processing module 72 may include one or more medication receptacles 100 used in the course of preparing a medical dose order. In this regard, the preparation of medical dose orders may be documented by capturing images of the medication receptacles 100 used to prepare the dose. The medical dose preparation images may be stored as metadata regarding the medical dose order. A medical dose preparation image may include one or more medication receptacles at various stages during the preparation of the dose. For example, a source receptacle, a transference receptacle, or an administration receptacle may be imaged before, during or after preparation of the dose.

The medical dose preparation images captured by the video data stream processing module 72 may be stored in a memory 120 in operative communication with the processor 70. In this regard, the medical dose preparation images may be stored locally in the memory 120 at the work station 40. Additionally or alternatively, the medical dose preparation images may be communicated to a remote location (e.g., an on-site medication dose order database 32 or an off-site medication dose order database 34 shown in FIG. 1) by way of a network interface 140 in operative communication with the processor 70. In any regard, medical dose preparation images may be accessible such that images may be later reviewed in the course of verifying (e.g., the verifying 62 described above in relation to FIG. 1) the medical dose order and/or for maintaining records regarding the dose orders prepared by the work station 40 and/or the hospital pharmacy 12 generally.

The processor 70 may also be in operative communication with a user control device 130. The user control device 130 may be operable to receive an input from a user (e.g., a pharmacy technician preparing a dose). The user control device 130 may be, for example, a foot pedal, a button, a touch screen, a mouse, a keyboard, or other user input device known in the art. A user may utilize the user control device 130 to trigger the capture of a medical dose preparation image from the video data stream 82. For example, a medication receptacle 100 may be viewed by the user by observing the display 110 displaying the video data stream 82 captured by the imaging device 80 of imaging field 86 including the medication receptacle 100. Once the image displayed on the display 110 is acceptable to the user, the user may use the user control device 130 to trigger the capture of the medical dose preparation image for storage in the memory 120 or in a remote database as described above.

The work station 40 may also include a printer 150 that is operative to print dose labels associated with a medical product, a dose that is in progress, and/or a completed dose. In this regard, the printer 150 may be a label printer operative to print labels used in the pharmacy 12 and/or hospital in connection with metal doses and/or medical dose orders.

Figure 3:
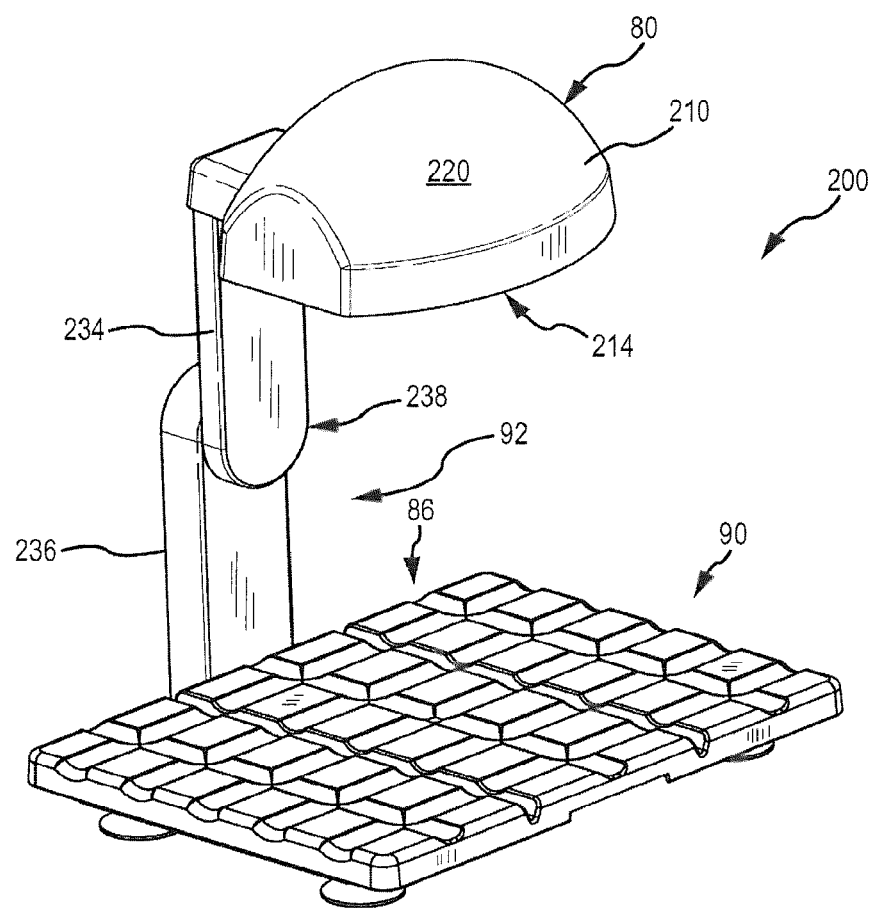
FIG. 3 is a perspective view of an embodiment of a camera stand of a work station.
Figure 4:
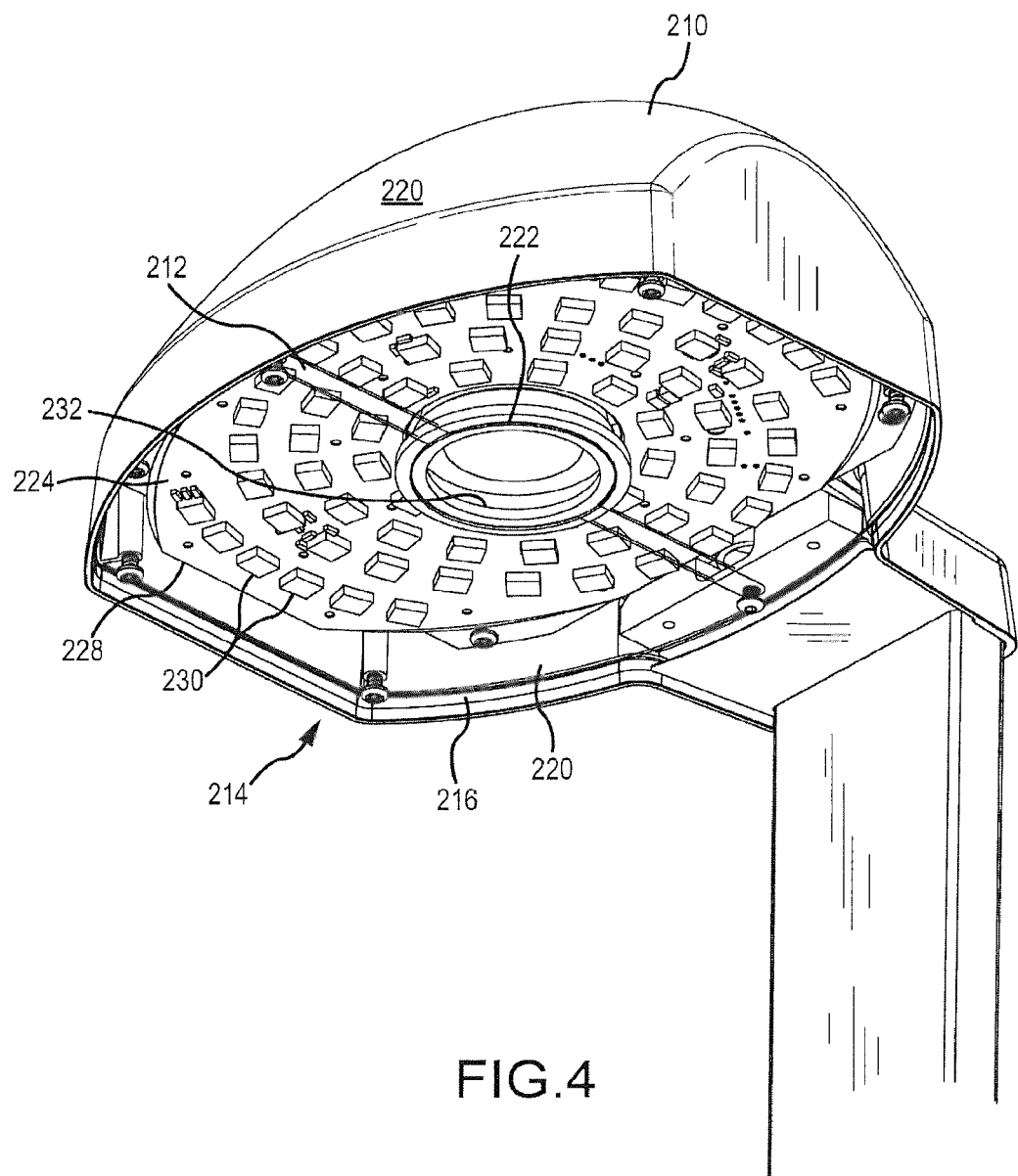
FIG. 4 is a perspective view of an embodiment of a housing of the camera stand of FIG. 3.
Figure 5:
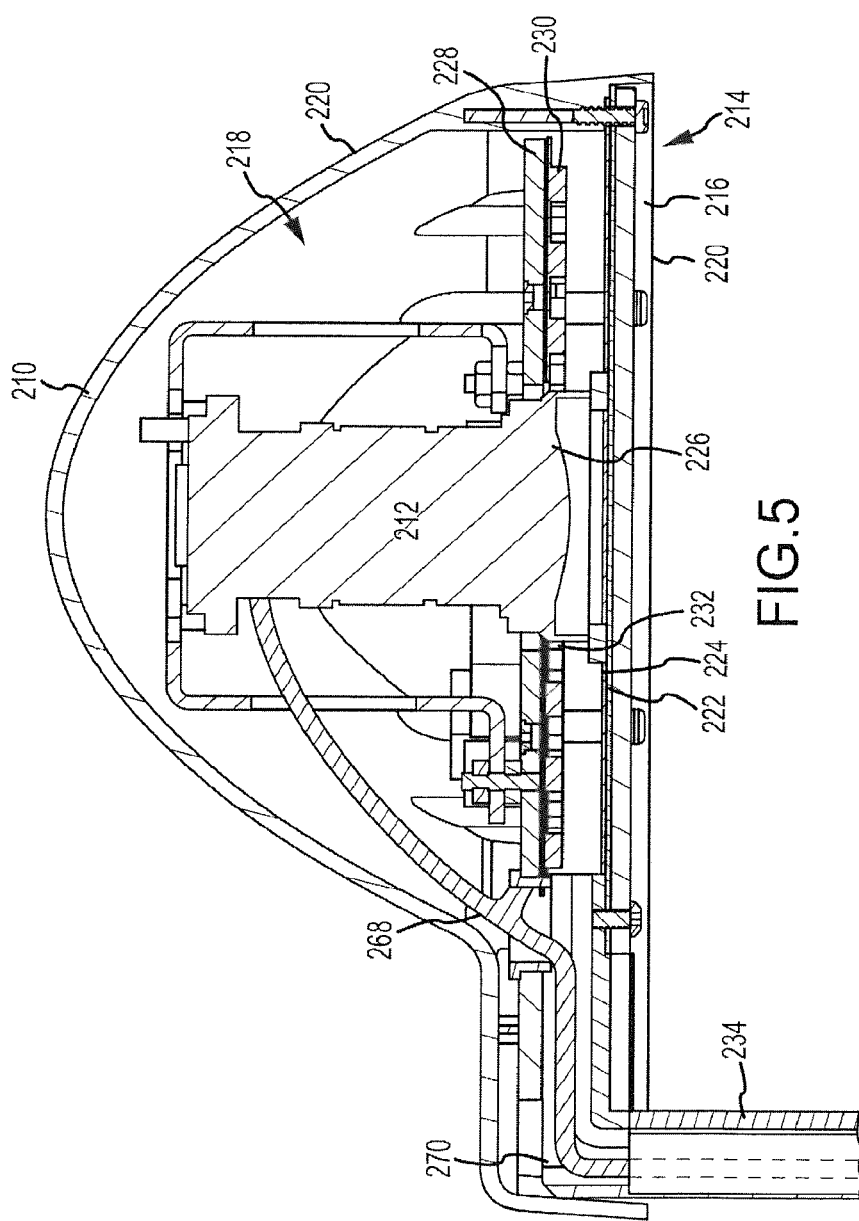
FIG. 5 is a cross-sectional view of the embodiment of the housing of the camera stand of FIG. 3 showing a camera and light sources disposed in an enclosed volume of the housing.

With further reference to FIG. 3, an embodiment of a camera stand 200 is depicted. As described above, the camera stand 200 may include an imaging device 80, a support 92, and a base 90. With respect to the imaging device 80, an imaging device housing 210 may contain a camera 212 (as shown in FIG. 5). With additional reference to FIGS. 4 and 5, the housing 210 may define an opening 214. The opening 214 may be disposed relative to the housing 210 such that the camera 212 may be directed through the opening 214 toward the medical dose preparation staging region 86. A transparent shield 216 may be disposed within the opening 214. For example, the transparent shield 216 may be secured to the housing 210.

The transparent shield 216 may extend across at least a portion of the opening 214 (e.g., in corresponding relation to the lens 226). In an embodiment, the transparent shield 216 may extend across substantially the entire opening 214. In this regard, the housing 210 and the transparent shield 216 may collectively define an enclosed volume 218 (best seen in FIG. 5) in which the camera 212 may be disposed. In this regard, the transparent shield 216 and housing 210 may also define a continuous outer surface 220 that extends about the enclosed volume 218. Accordingly, the continuous outer surface 220 may allow for easy cleaning of the housing 210 and the transparent shield 216. For example, the continuous outer surface 220 may be wipeable by an operator to facilitate cleaning. As the continuous outer surface 220 may be resistant to fluids penetrating the enclosed volume 218, the components disposed within the enclosed volume 218 may remain dry when the outer surface 220 is exposed to fluids (e.g., cleaning products). Further aspects of the camera stand 200 discussed below may also assist in the cleaning of a work station 40.

Also disposed within the enclosed volume 218 may be a light source board 228. The light source board 228 may include one or more light sources 230 connected to the light source board 228. The light sources 230 may comprise individual light emitting diodes (LED). The light sources 230 may be attached to the light source board 228 such that power and/or control signals used in the operation of the light sources 230 are provided to the light sources 230 by way of the light source board 228. In this regard, the light source board 228 may provide a physical mounting substrate for supportably engaging the light sources 230 as well as providing electrical communication between the light sources 230 and the light source board 228. In this regard, the light source board 228 may be a printed circuit board (PCB) including attachment locations and appropriate electrical communication paths (e.g., conductive traces) to facilitate attachment and electrical communication between the light sources 230 and the light source board 228.

The light source board 228 may include an aperture 232. A lens 226 of the camera 212 may be aligned with the aperture 232 such that an imaging field 84 of the camera 212 defined by the lens 226 extends through the aperture 232. The aperture 232 may also be aligned with a central region of the opening 214 of the housing 210. As such, a peripheral region extending about the central region of the opening 214 may be occupied by the light source board 228, and thus the light sources 230. In this regard, the light sources 230 may be provided peripherally about the aperture 232 of the light source board 228, and thus the lens 226 of the camera 212. The light sources 230 may emit light through the opening 214. As such, the light emitted from the light sources 230 may at least partially coincide with the imaging field 84 of the camera 212. In this regard, the distribution of the light sources 230 as shown in FIG. 4 where the light sources 230 are distributed through the peripheral region of the opening 214 about the lens 226 and aperture 232 may facilitate the relatively uniform distribution of light from the light sources 230.

With further reference to FIG. 5, the camera 212 may be contained in the enclosed volume 218 defined by the housing 210 and the transparent shield 216.

As can further be appreciated in FIG. 5, one or more polarization filters 222 and 224 may be provided. As depicted, a peripheral polarization filter 222 and a central polarization filter 224 may be provided. At least a portion of the peripheral polarization filter 222 and at least a portion of the central polarization filter 224 may be disposed in non-overlapping relation. For example, the peripheral polarization filter 222 may be disposed in the peripheral region of the opening 214 in corresponding relation to the light source board 228 and the light sources 230. The central polarization filter 224 may be disposed in the central region of the opening 214 in corresponding relation to the lens 226 of the camera 212.

In this regard, the peripheral polarization filter 222 and the central polarization filter 224 may be disposed such that the direction of polarization of the filters are oriented perpendicularly to each other.

Accordingly, as light is emitted from the light sources 230, the emitted light may pass through the peripheral polarization filter 222 and, thus, be polarized according to the first direction of polarization associated with the peripheral polarization filter 222. The light may then travel toward the medical dose preparation staging region 86, which may become illuminated by the emitted light polarized in the first direction. The emitted light originating from the light sources 230 may be reflected from the medical dose preparation staging region 86. In turn, the emitted light may then pass through the central polarization filter 224, where the reflected light is then polarized in a second direction of polarization by the central polarization filter 224 that is perpendicular to the first direction of polarization associated with the polarization filter 222. In this regard, light emitted from the housing 210 may be polarized in the first direction of polarization by the peripheral polarization filter 222, be reflected back from the medical dose preparation region 86 such that the polarization of at least some of the light is changed, and be polarized in the second direction of polarization by the central polarization filter 224. The result may be reduced glare on objects placed in the medical dose preparation staging region 86. For example, especially in the case of shiny materials such as glass, light that impinges on an object in the medical dose preparation staging region 86 normal to the surface may not undergo a change in polarization. Thus, the light incident normal to the object that may result in glare does not change in polarization from the first direction. The introduction of the central polarization filter 224 with a polarization in the second direction may fully block the reflected light that is still in the first polarization direction because the light was reflected normal to the surface, thus reducing the glare the light in the first polarization direction may otherwise produce.

Figure 6:
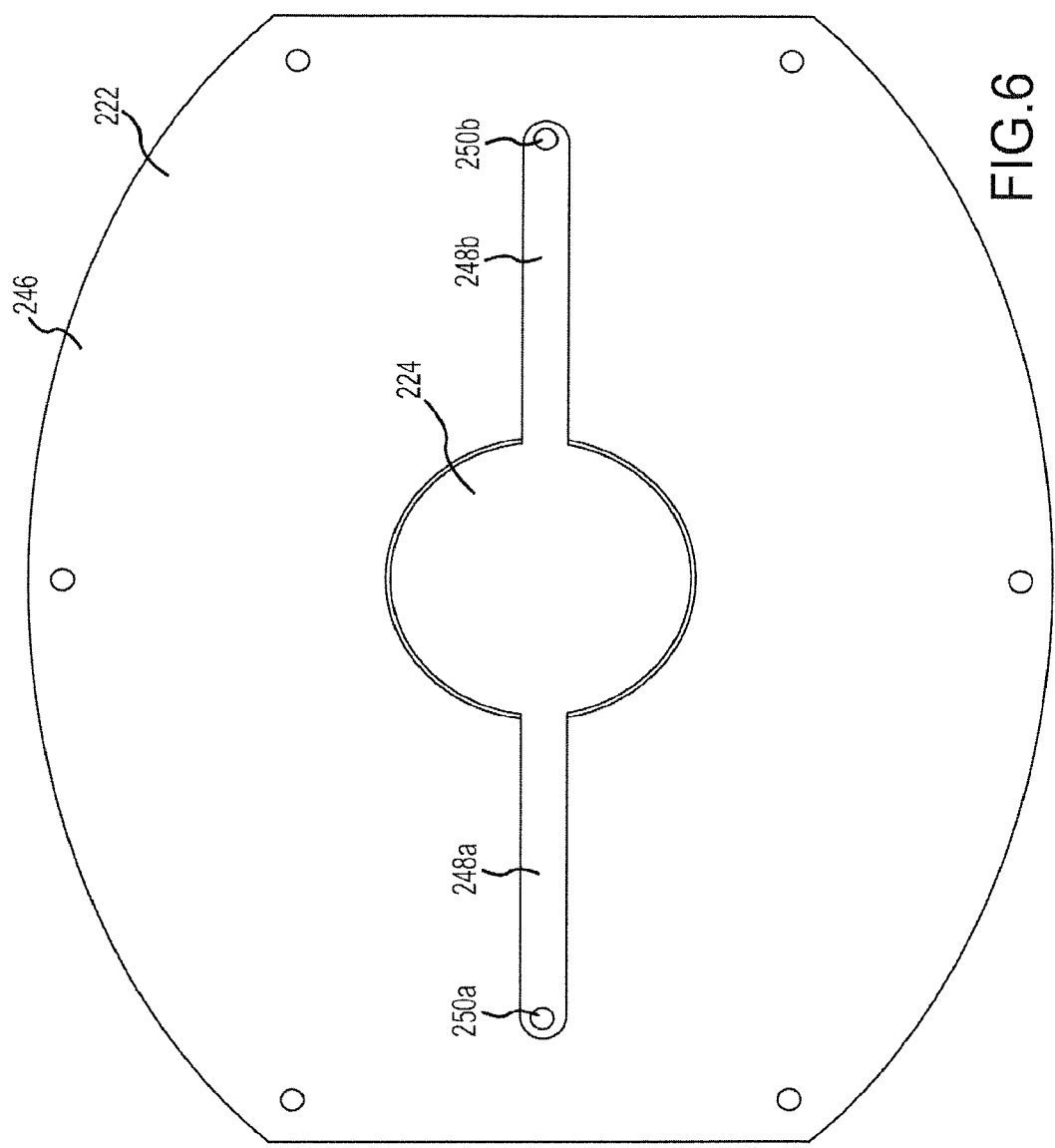
FIG. 6 depicts an embodiment of a polarization filter during production of the polarization filter.
Figure 7:
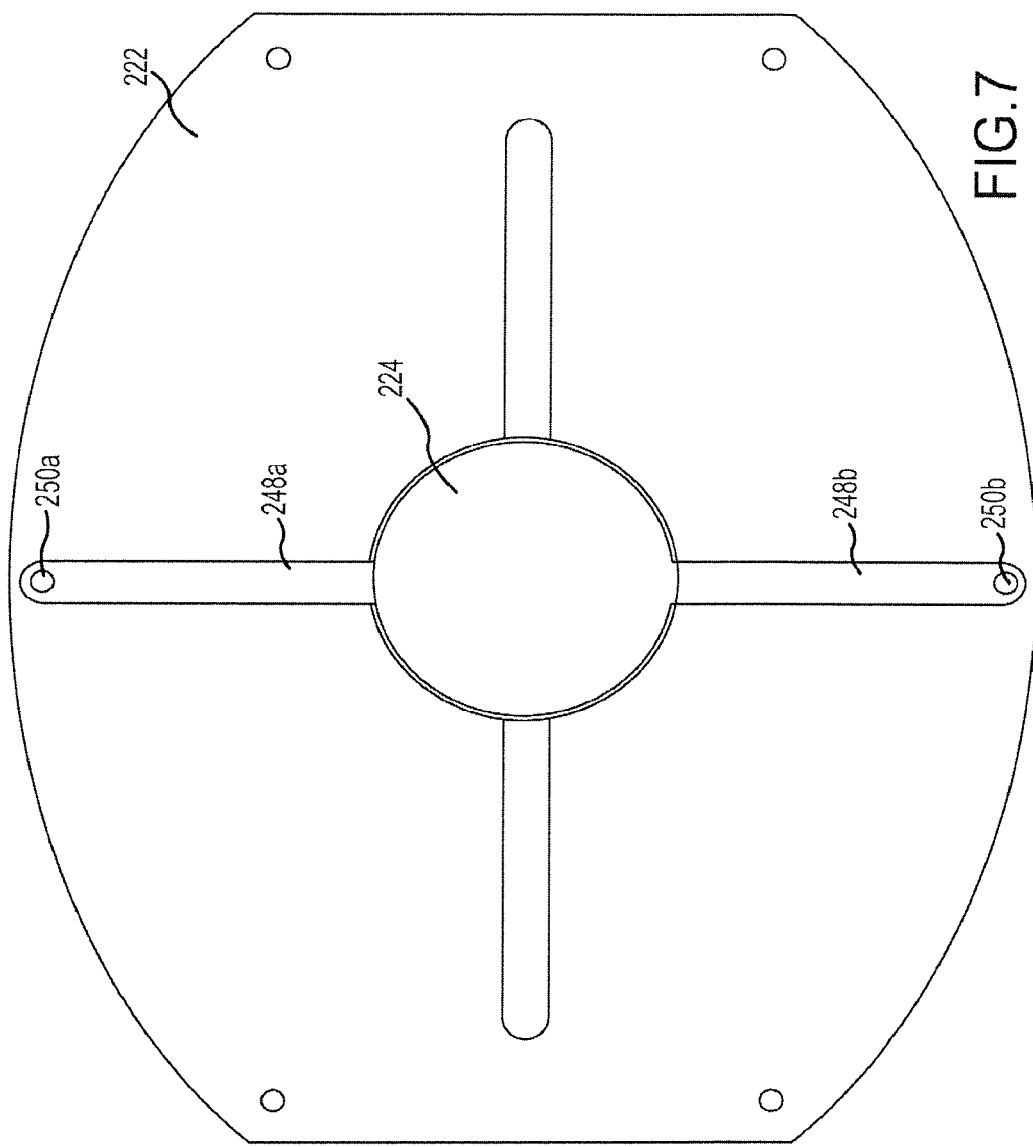
FIG. 7 depicts the embodiment of the polarization filter of FIG. 6 in a finished and aligned state.

To achieve the foregoing relative orientations of the polarization of the peripheral polarization filter 222 and the central polarization filter 224, the respective filters may be manufactured from a unitary sheet of polarized material. With respect to FIG. 6, the central polarization filter 224 may be cut from a unitary sheet of polarizing material 246 with a single polarization orientation. The central polarization filter 224 may include wings 248a and 248b, each having a mounting hole 250a and 250b, respectively. With further reference to FIG. 7, once the central polarization filter 224 has been separated from the unitary sheet of polarizing material 246, it may be rotated 90° relative to the remainder of the unitary sheet of polarizing material 246 now comprising the peripheral polarization filter 222. In this regard, the polarization directions of the central polarization filter 224 may be perpendicular to the peripheral polarization filter. Furthermore, the separation of the central polarization filter 224 from the peripheral polarization filter 222 may provide the non-overlapping relation between the central polarization filter 224 and peripheral polarization filter 222 (e.g., with the exception of the wings 248a and 248b of the central polarization filter 224). In other embodiments, completely separate portions may be provided that define the central polarization filter 224 and the peripheral polarization filter 222. As such, the polarization directions of the separate portions may be tested and aligned appropriately to achieve perpendicular relative orientations of the polarization directions.

Additionally or alternatively, other optical filters may be provided other than the polarization filters described above. For example, a diffusion filter may be provided that may provide more uniform light distribution at the medical dose preparation staging region 86. Other optical filters such as high pass, low pass, band pass, or any other appropriate optical filters may be employed to selectively control the emission of light from the light source. Additionally, light sources that emit certain wave length light may also be employed. Further still, light sources may be employed that are operable to controllably emit different wave length light (e.g., the color of the light may be controlled).

It may be appreciated in FIG. 5 that the camera 212 is contained in the enclosed volume 218. In this regard, access to the camera 212 may be limited. Accordingly, optical settings associated with the camera 212 may not be modifiable by a user by manipulation of the camera 212 directly. It has been found that often in an effort to improve image quality, an operator may adjust the optical settings of a camera 212. However, the resulting adjustments may ultimately degrade the quality of images resulting in suboptimal focus and/or aperture settings for a variety of images to be captured using the camera 212.

Accordingly, in an embodiment, the camera 212 includes at least one fixed optical setting. For example, one or more optical settings may be fixed such that a depth of field of the camera 212 as defined by the lens 226 encompasses at least a portion of the medical dose preparation staging region 86. In an embodiment, at least a majority of the medical dose preparation staging region 86 is encompassed by a depth of field of the camera 212. In an embodiment, substantially all of the medical dose preparation staging region 86 is encompassed by a depth of field of the camera 212. The fixed optical settings of the camera 212 may comprise a focus setting, an aperture setting, a magnification, or another optical setting affecting the depth of field of the camera 212.

In another embodiment, the optical settings of the camera 212 may be adjustable (e.g., by a user). For example, a focal length, magnification, or other optical parameter of the camera 212 may be adjusted. The adjustment of the optical settings may be manually accomplished by a user manipulating a portion of the camera 212. In an application, an electronic signal may be provided to the camera 212 in order to adjust the optical settings thereof. In an embodiment, camera 212 may be continuously adjustable through a continuum of settings associated with one or more optical parameters. In another embodiment, a plurality of discrete optical parameters may be selectable. For example, the optical parameters the camera 212 may be selected from among at least two different optical parameter settings. For example, a corresponding optical parameter setting may be selected based on a selected position of the camera 212 relative to the base 90. In this regard, the camera 212 may be disposed at different distances relative to the base for different positions of the support 92 and/or for different configurations of the camera stand 200. In this regard, for the various different configurations available, discrete optical setting may be provided for each position of the imaging device 80 relative to the base 90 such that the optical parameters associated with the camera 212 results in a clear image of the medication receptacle 100 being imaged by the camera 212.

In an embodiment, the light sources 230 may be used to indicate when a medical dose preparation image has been captured. That is, as described above, a user control device 130 may be used to initiate the capture of a medical dose preparation image from a video data stream 82. In a first predetermined period after the capture of the medical dose preparation image, the intensity of at least one of the light sources 230 may be changed. The change in intensity may indicate to the user that the image has successfully been captured. In this regard, the light intensity of the light source 230 may change from a default level to a modified intensity (e.g., either more or less intense). The light source 230 may then return to the default intensity after a second predetermined period of time. In this regard, the light source 230 may "blink" or "flicker" or momentarily change from the default intensity to a modified intensity and then return to the default intensity). The variation in intensity may be readily perceived by a user to indicate the image has been captured and that the medical dose preparation staging region 86 may be cleared and, for example, prepared for the next image.

Returning to FIG. 3, the housing imaging device 80 may be supportably engaged by a support 92. The support 92 may allow for selectively positioning the support 92 in at least a first position and a second position relative to the medication preparation staging region 86. For example, the support 92 may be selectively positionable between the orientation shown in FIG. 3 (referred to herein as a first position) and that shown in FIGS. 8 and 9 (referred to herein as a second position).

In this regard, the support arm 92 may include a first portion 234 and a second portion 236. The first portion 234 may be supportably engaged with the housing 210 and the second portion 236 may be supportably engaged with the base 90. The first portion 234 may be positionably attached to the second portion 236 at a connection 238. For example, the first portion 234 may be moveably attached to the second portion 236 such that the first portion 234 may undergo relative movement with respect to the second portion 236 to move between the first position depicted in FIG. 3 and the second position depicted in FIG. 10. In this regard, the connection 238 may comprise a hinge to provide pivotal movement between the first portion 234 and the second portion 236 between the first position and the second position.

The movement of the first portion 234 relative to the second portion 236 may be dampened and/or dampenable. In this regard, connection 238 may include a dampener that dampens movement of the first portion 234 relative to the second portion 236. In one embodiment, the dampener may comprise coordinating elliptical profiles provided on each of the first portion 234 and the second portion 236 at the connection 238. The elliptical profiles may be provided as coordinating surfaces of the first portion 234 and the second portion 236. Other shaped profiles may be provided other than elliptical profiles such as, for example, a non-uniform contoured shape (e.g., profile defining one or more cam lobes).

Figure 10A:
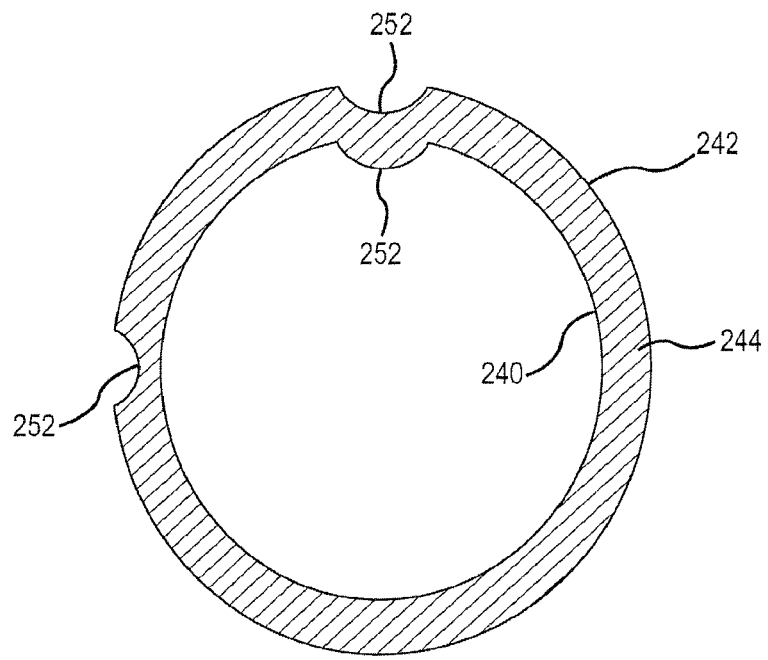
FIGS. 10A and 10B depict an embodiment of a connection between a first portion and a second portion of a support in a first position and a second position, respectively.
Figure 10B:
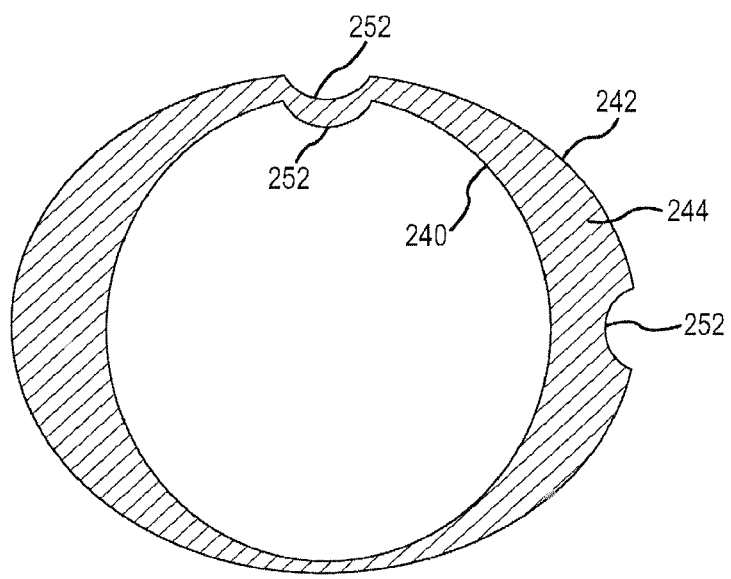
Figure 11:
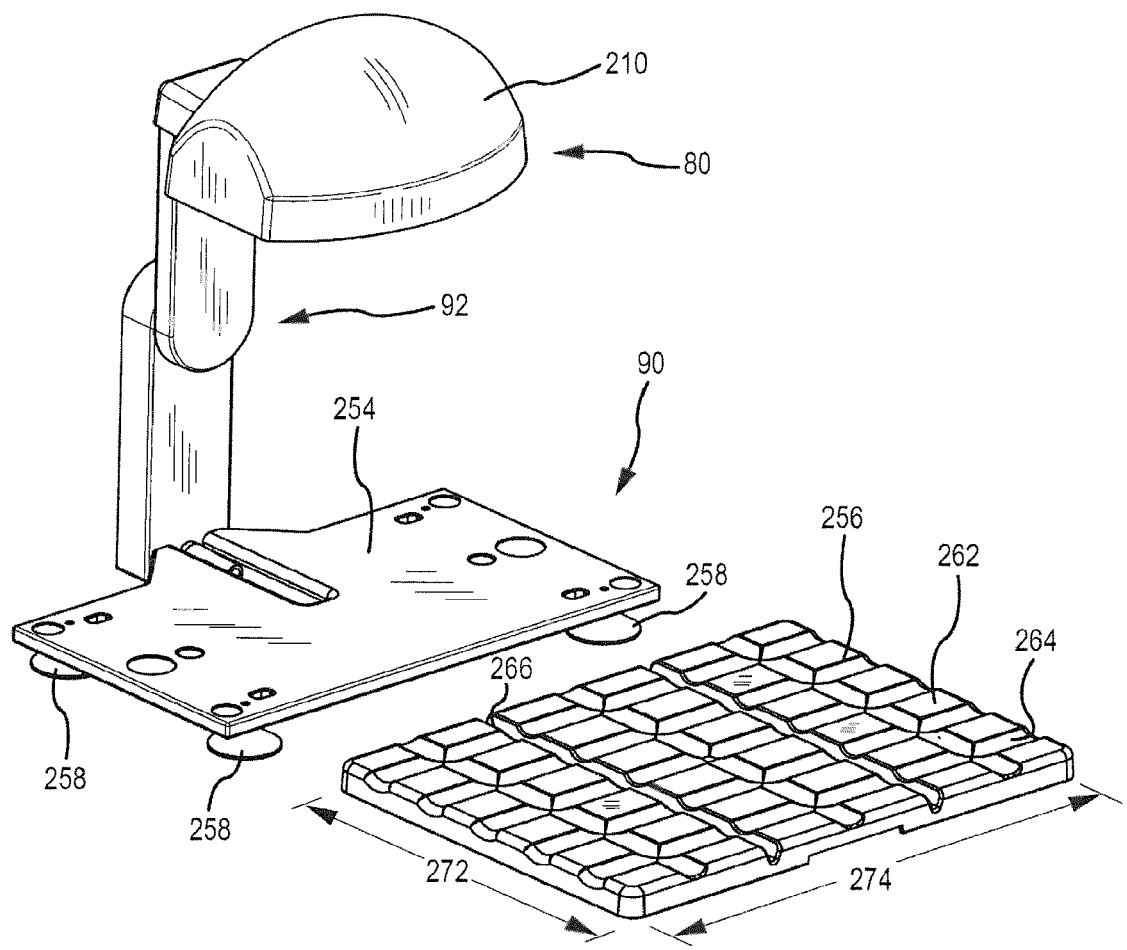
FIG. 11 is a perspective view of a base of the camera stand of FIG. 3 with a support platform in a removed position.

One embodiment illustrating the use of coordinating elliptical surfaces to achieve dampened movement between the first portion 234 and the second portion 236 is shown in FIGS. 10A and 10B. For example, a first elliptical surface 240 may be provided on the first portion 234 and a second elliptical surface 242 may be provided on the second portion 236. The elliptical surfaces 240 and 242 may be concentrically disposed and separated by a resilient material 244 (e.g., a resilient o-ring or the like). Upon pivotal movement of the first portion 234 relative to the second portion 236, the elliptical surfaces 240 and 242 may converge, resulting in compression of the resilient material 244, thus dampening movement between the first portion 234 and the second portion 236. Also, coordinating detent features 252 may be provided for registration of the first portion 234 relative to the second portion 236 at the first position 234 and the second position 236. The damping may be non-uniform through the movement of the first portion 234 and the second portion 236. For example, the damping force acting in response to movement between the first portion 234 and the second portion 236 may be less as the first portion 234 and the second portion 236 move toward the first position (shown in FIG. 3). Thus, the positioning of the first portion 234 relative to the second portion 236 may be more precise given the damping force is less near this point than at other points of travel between the first portion 234 and the second portion 236.

Figure 8:
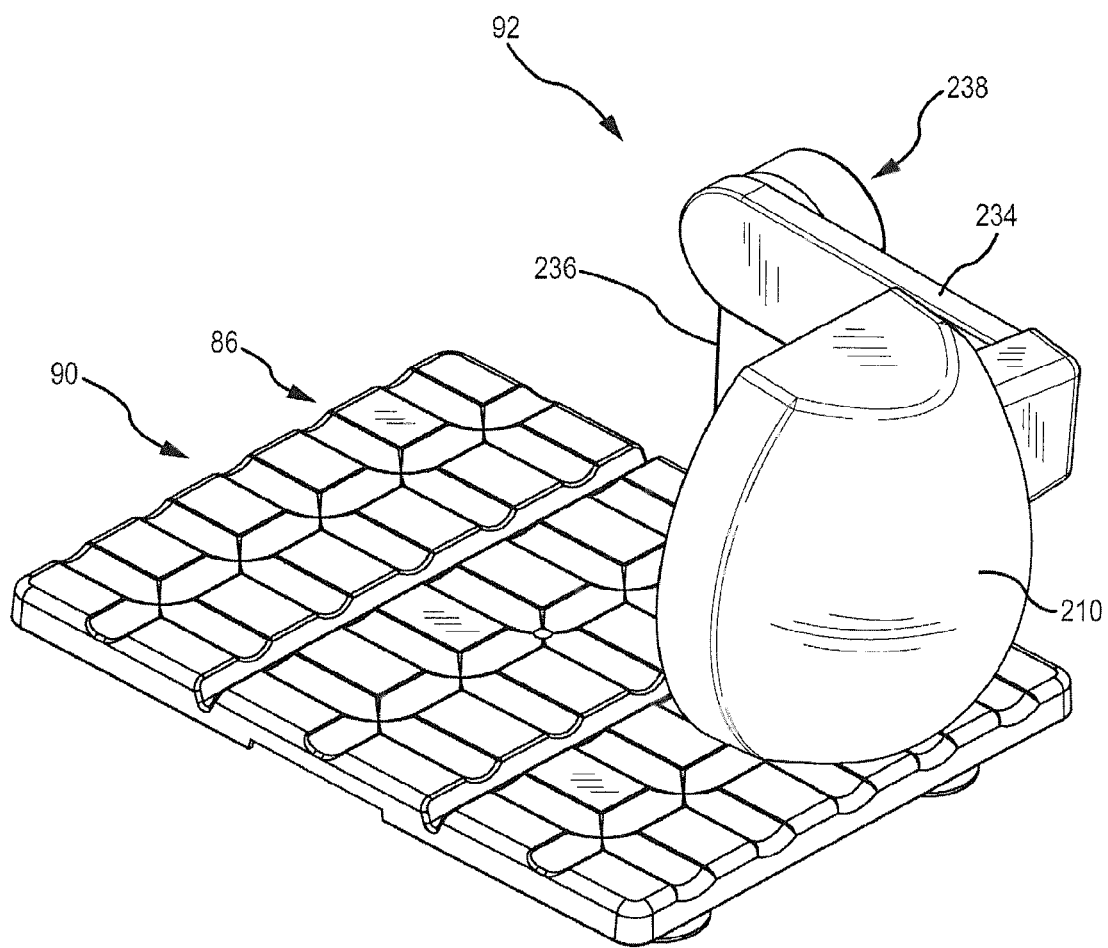
FIG. 8 is a perspective view of the embodiment of the camera stand of FIG. 3 with a support disposed in a second position.
Figure 9:
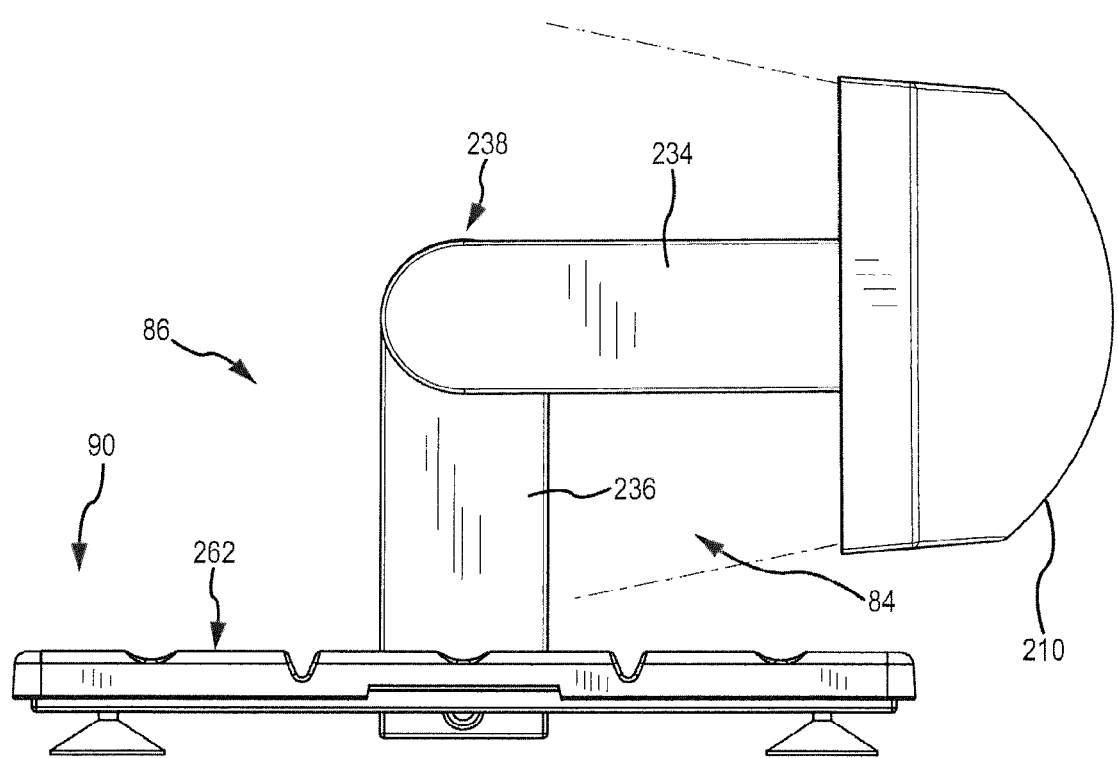
FIG. 9 is a plan view of the embodiment of the camera stand of FIG. 3 with the support disposed in the second position.

As may be appreciated in FIGS. 3 and 8-9, the first position (shown in FIG. 3) of the support 92 may dispose the imaging device 80 such that the imaging field 84 of the imaging device 80 is oriented in a manner such that the medication preparation staging region 86 is disposed between the imaging device 80 and the base 90. That is, the camera 212 may be directed at the base 90 such that the medication preparation staging region 86 defined by the base is between the camera 212 and the base 90 and in the imaging field 84 of the camera 212. In this regard, a medical dose preparation image captured by the camera 212 may include an image whose dimensions correspond to a length and width of the medication preparation staging region 86.

In the second position (shown in FIG. 10) the imaging device 80 may be oriented with respect to the base 90 such that the imaging field 84 of the imaging device 80 extends parallel to a plane defined by a support surface 262 of the base 90 that is described in greater detail below. That is, the camera 212 may be directed perpendicularly to the base 90 such that the imaging field 84 extends in a direction parallel to the support surface of the base to encompass at least a portion of the medical dose preparation staging region extending normal to the base 90.

The support 92 may also contain at least a portion of an umbilical 268 that may be operable to establish communication between the components disposed in the enclosed volume 218 (e.g., the camera 212, the light source board 228, light sources 230, etc.). In this regard, the umbilical 268 may establish electrical communication paths between the components in the enclosed volume 218 and the processor 70. In some embodiments, the umbilical 268 may include one or more bundled or consolidated cables, one or more conductive traces, a plurality of wires, or other appropriate conductors to establish electrical communication between the components in the enclosed volume 218 and the processor 70. As shown in FIG. 3, the umbilical 268 may extend from the camera 212 and/or the light source board 228 and pass into a passage 270 defined in first portion 234. The passage 270 may extend from the first portion 234 to the second portion 236. In this regard, the connector 238 may facilitate passage of the umbilical 268 therethrough. For example, the umbilical 268 may pass through the second portion 236 and emerge therefrom. The umbilical 268 may include a connector at an end opposite that in communication with the components in the enclosed volume 218 that may be used to establish electrical communication with the processor 70. For example, the connector may be a proprietary or standard connector (e.g., a USB connector or the like).

It may be noted that the umbilical 268 may provide electrical communication paths for a plurality functions. For example, signal paths and/or power communication paths may be provided in the umbilical 268. In this regard, plurality of discrete electrical communication paths may be consolidated into a single cord extending from the camera support 200. In the context of a work station 40, the minimization of wires in the work area may provide advantages, especially in the context of cleaning the workstation 40. That is, the fewer wires present in a work area (such as a laminar flow hood, isolator, or biological safety cabinet) the easier the work station 40 may be to clean.

Furthermore, in the context of, for example, a biological safety cabinet, it may be appreciated that elimination of wires or cables extending from the camera stand altogether may be particularly advantageous. For example, a biological safety cabinet may provide complete isolation from an external environment. In this regard, should a camera stand 200 include a cord, the cord may be required to pass through the wall of the biological safety cabinet. However, a minimum level of containment must also be maintained, which may be difficult or costly to achieve while facilitating passage of the cord through the cabinet wall. In this regard, it is contemplated that the camera stand 200 may be completely wireless. For example, wireless technology may be incorporated to the camera stand 200 to facilitate communication of electronic signals between the camera stand 200 and the processor 70. Examples of such wireless technology include Wi-Fi, Bluetooth, or other wireless vacation technologies. Furthermore, the camera stand 200 may be equipped with a battery to provide operational power to the camera stand 200. The battery may be removable, replaceable, and/or rechargeable to facilitate wireless operation of the camera stand 200. For example, a lithium-ion battery or other appropriate type of battery may be provided in the camera stand 200. The battery and provided any portion of the camera stand 200 without limitation including for example, the base 90, the support 92, and/or the enclosed volume 218.

Figure 15:
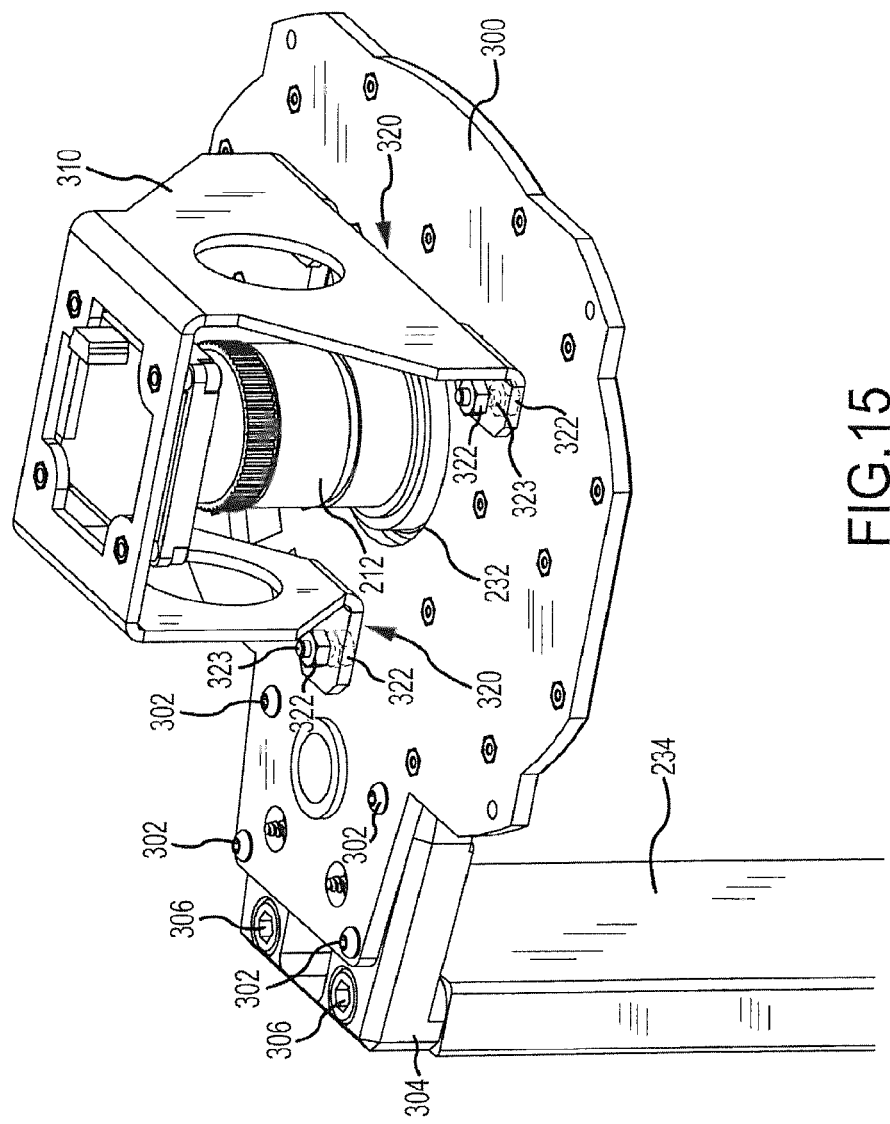
FIG. 15 is a perspective view illustrating an embodiment of an attachment of an imaging device to a support.

With further reference to FIG. 15, a mechanism for attaching the camera 212 to the first portion 234 of the support 92 is shown. It may be appreciated that the camera 212 may be subject to an image tolerance associated with the alignment of the camera 212 to the base 90. Misalignment between the camera 212 in the base 90 may result in image distortion such as keystoning or the like. In this regard, the image tolerance associated with the alignment between the camera 212 of the base 90 may be important to obtain quality medical dose preparation images using the camera 212. However, manufacturing considerations associated with providing connection tolerances between various pieces comprising the camera stand 200 may make it difficult to achieve the image tolerance to provide accurate camera alignment during manufacturing. That is, the camera 212 may include an imaging tolerance that is more restrictive than the connection tolerances provided in the attachment of the camera 212 to the camera stand 200. For example, connection tolerances may be introduced, inter alia, at the interface between the base and second portion 236 of the support 92, the first portion 234 and the second portion 236, the attachment of a mounting plate 300 and the first portion 234, and the interface to the camera 212 and associated mounting structure. Furthermore, it may be appreciated that the tolerances associated with each of these interfaces may present a tolerance stack up problem that may result in misalignment of the camera 212 with respect to the base 90.

Accordingly, as depicted in FIG. 15, a mounting plate 300 may be secured by way of fasteners 302 to an attachment member 304. The attachment member 304 may be secured to the first portion 234 by way of fasteners 306. A mounting structure 310 may be secured to the mounting plate 300. The camera 212 may be mounted to the mounting structure 310. The interface between the mounting structure 310 and the mounting plate 300 may define a gimbal 320. The gimbal 320 may allow for adjustable movement of the camera 212 in at least a first (and potentially two, three, or more) directions. The gimbal 320 may include one or more jack nuts 322 that may allow the mounting structure 310 to be adjustably positioned relative to the mounting plate 300. For example, the jack nuts 322 may include coordinating nut pairs provided on a threaded stud 323 such that the attachment of the mounting structure 310 relative to the mounting plate 300 may be adjusted up and down along the threaded studs 323 (e.g., at three locations as shown in FIG. 15 to control movement of the camera 212 in at least two directions) Accordingly, the camera 212 may be adjusted or aimed by manipulating the jack nuts 322 to modify the orientation of the camera 212 once secured to the mounting structure 310.

In this regard, it may be appreciated that once the attachment member 304 is secured to the first portion 234, the mounting plate 300 is secured to the attachment member 304, the mounting structure 310 is secured to the mounting plate 300, and the camera 212 secured to the mounting structure 310, the alignment of the camera 212 may be non-perpendicular to the base 90 (i.e., the imaging tolerance may not be achieved). In this regard, the jack nuts 322 may be manipulated so as to align the camera 212 to be substantially perpendicular to the base 90 such that any image distortion such as keystoning may be eliminated from the resultant image obtained by camera 212. In other words, the imaging tolerance may be achieved via adjustment of the gimbal 320. As such, the amount of adjustment provided by the gimbal 320 may at least correspond to the difference between the connection tolerance and the imaging tolerance associated with the alignment of the camera 212 to the base 90.

It may be appreciated that the mounting plate 300 and/or mounting structure 310 may be fabricated from sheet material. In this regard, the manufacturer of these components may be provided at significant lower cost than other manufacturing techniques that may be employed when tolerances are required to be relatively high. In this regard, the use of the gimbal 320 provide adjustability of the alignment of the camera 212 once secured to a mounting structure may allow for manufacturing techniques that are less costly to be employed when manufacturing the camera stand 200.

While not shown in FIG. 15, it may be appreciated that the housing 210 and/or transparent shield 216 may be secured to the mounting plate 300 and/or mounting member 304. In this regard, the housing 210 and/or transparent shield 216 may be secured relative to the mounting plate 300 and/or mounting member 304 to define the enclosed area 218.

Figure 12:
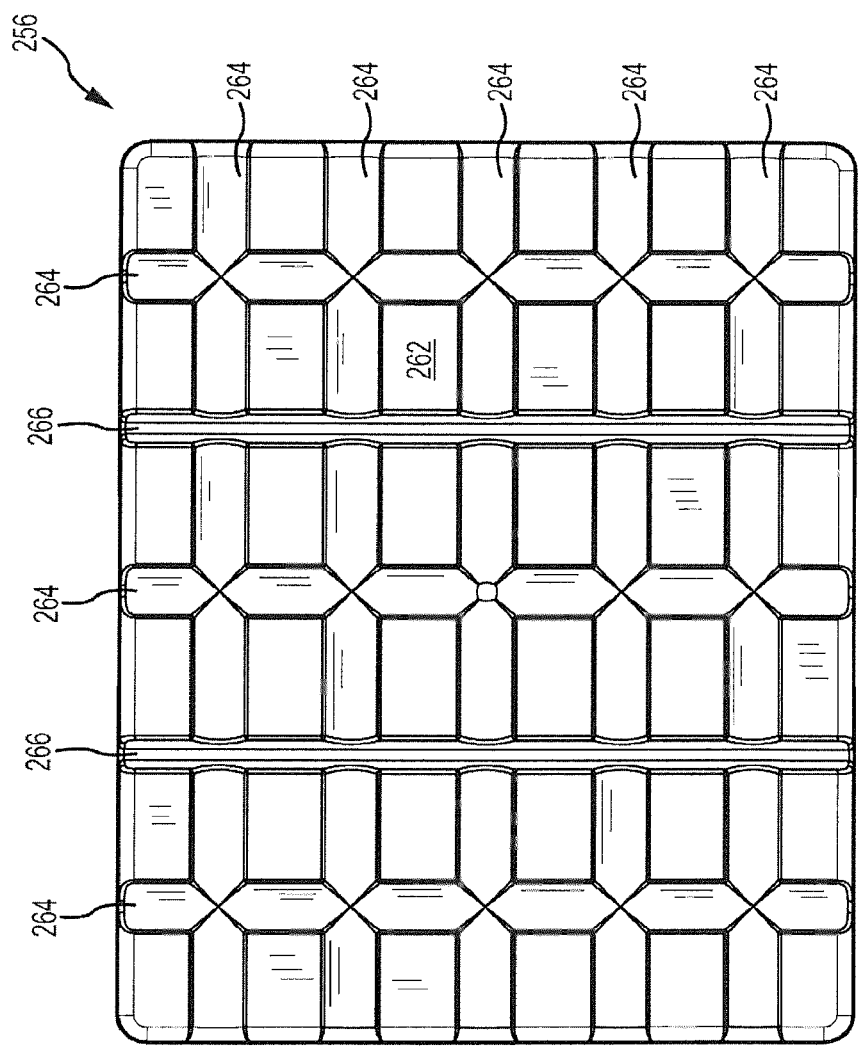
FIG. 12 is a top view of an embodiment of a support surface of a work station.

With further reference to FIG. 12, the base 90 of the camera stand 200 may include a platform base 254 and a support platform 256 that is removably disposable relative to the platform base 254. In this regard, the support platform 256 may be removed, for example, to undergo cleaning or the like. The platform base 254 may include one or more feet 258 that may engage a surface on which the platform base 254 is disposed. For example, the platform-based 254 may include one or more suction cup bases 276 may be used to secure the base 90 and in turn the camera stand 200 to the surface. The suction cup bases 276 may provide secure attachment to the surface to provide stable operation of the camera stand 200. That is, suction cup bases 276 may at least partially isolate vibrations to improve the image obtained by the camera 212 when capturing a medical dose preparation image as described above. The support platform 256 may be constructed of a UV resistant material.

The support platform 256 may have a length 272 and a width 274. In this regard, when the support platform 256 is disposed on the platform base 254, the length 272 and width 274 may define dimensions of the base 90. The length 272 and the width 274 may also correspond to a medical preparation staging region 86 at least partially defined by the support platform 256.

Additionally, with reference to FIG. 4, it may be appreciated that the peripheral region of the opening 214 of the housing 210 may extend in a first direction corresponding to the length 274 of the support platform 90. The peripheral region may extend in the first direction corresponding to the length 274 of the base 90 both when the support 92 is in the first position shown in FIG. 3 and the second position shown in FIGS. 8-9. The peripheral region may extend in a second direction corresponding to the width 274 of the support platform 256 when the support 92 is in the first position. When the support is in the second position (as best seen in FIG. 9), the peripheral region may extend in a direction corresponding to a height of the medical dose preparation region 86 extending normal to the support platform 256.

The platform base 254 may include a scale such that an item disposed on the support platform 256 when disposed on the platform base 254 may be weighed. For example, the weight measured by the scale may be captured substantially simultaneously as the capture of a medical dose preparation image by the imaging device 80. Accordingly, the weight obtained by the scale may be appended to the dose order metadata. In an embodiment, the processor 70 at the processor or a remote processor with access to the metadata may perform a gravimetric analysis using a weight measured by the scale to, for example, compare the measured weight to an anticipated weight for the medical dose. The scale may comprise load cells disposed in the platform base 254 (e.g., at each foot 258 of the platform base 258 or adjacent to where the support platform 256 is supported.

In this regard, the anticipated weight for the medical dose may be contained in the metadata to assist in a gravimetric analysis of the medication receptacle 100. The processor 70 at the work station 40 may associatively store the anticipated weight and the measured weight. Furthermore, the processor may be operable to compare the measured weigh to the anticipated weight. In an embodiment, a deviation of the actual weight from the anticipated weight may be calculated and if the deviation exceeds a threshold, an alarm may be provided to the user.

The support platform 256 may at least partially define the medication preparation staging region 86. For example, the medication preparation staging region 86 may encompass a volume extending in a direction normal to a support surface 262 of the support platform 254. As such, a receptacle supportably engaged by the support platform 254 may be encompassed by the medication preparation staging region 86 such that the receptacle is disposed in the imaging field of the imaging device 80.

Figure 13:
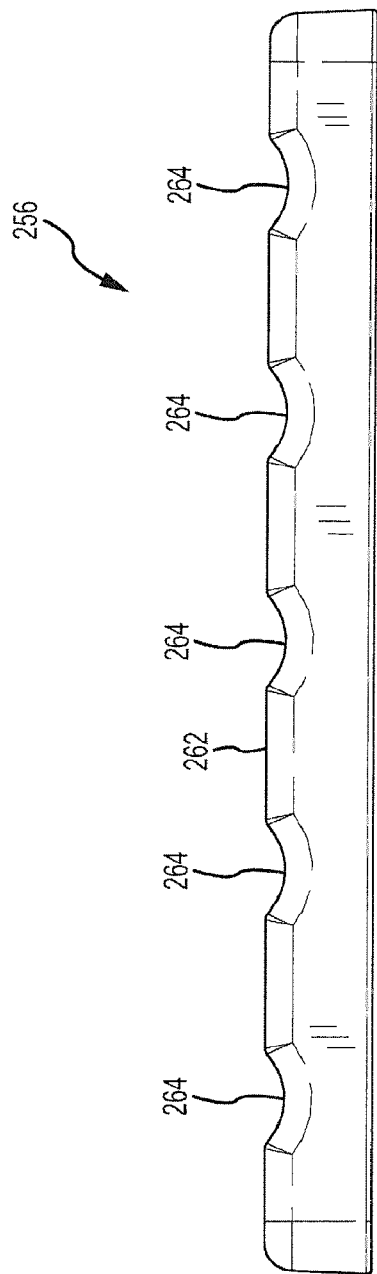
FIGS. 13 and 14 are front and side views, respectively, of the support surface of FIG. 12.
Figure 14:
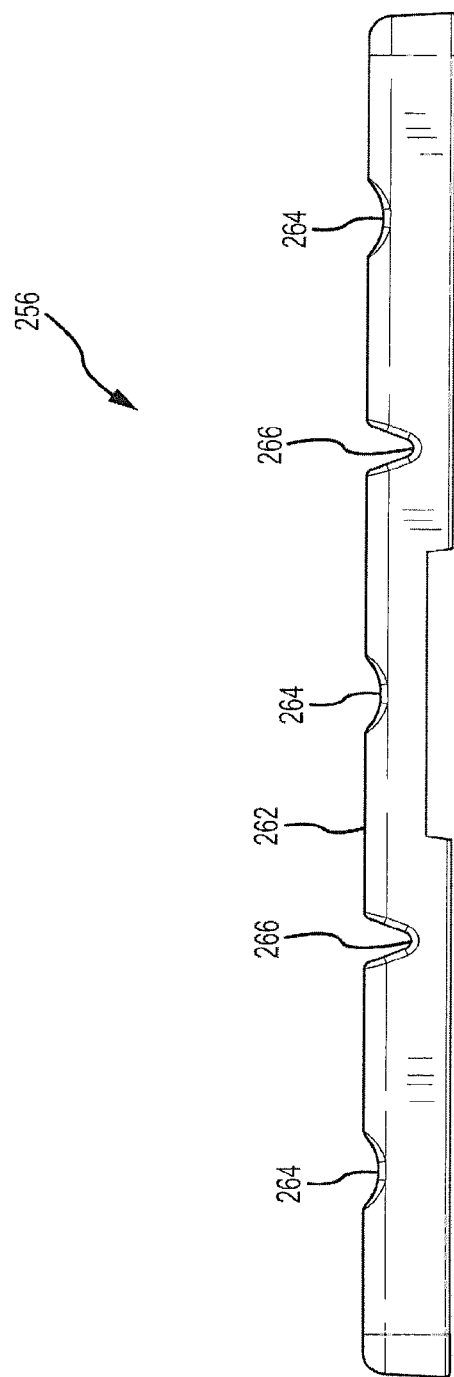

The support platform 254 may also include one of more medication receptacle engagement feature that may engage a medical receptacle that is supportably disposed with respect to the support platform 254. For example, the medication receptacle engagement features may include at least one groove 264 and at least one channel 266. With further reference to FIGS. 13-15, the features described comprising the support platform 254 may be further appreciated. The grooves 264 may extend from the support surface 262 a first depth. The channels 266 may extend from the support surface 262 a second depth. The first depth may be less than the second depth. That is, the grooves 264 may be shallower with respect to a depth extending from the support surface 262 than the channels 266. The engagement features described herein may extend across substantially all of the support platform 254, and in turn, the medication preparation staging region 86 at least partially defined by the support platform 254. In an embodiment, at least a portion of the grooves 264 extend in a direction different than at least a portion of the channels 266. For example, at least a portion of the grooves 264 may extend perpendicularly to the channels 266. In addition, at least a portion of the grooves 264 may extend in a direction corresponding to the channels 266.

The grooves 264 may have a first radius of curvature in a direction corresponding to the first depth from which the grooves 264 extend from the support surface 262. In this regard, the grooves 264 may have a generally concave profile. For example, a concave surface profile may be defined along the groove 264. Similarly the channel 266 may include a second radius of curvature in a direction corresponding with the second depth. In this regard, the channels 266 may also have a generally concave profile (e.g., a concave surface profile). The first radius of curvature may be larger than the second radius of curvature such that the grooves 264 include a shallower profile versus a steeper profile of the channels 266.

In an embodiment, the grooves 264 may be adapted to engage a first portion of a medication receptacle. For example, the concave surface profile of the grooves 264 may correspond with the circumference of the barrel of a syringe. In this regard, the syringe barrel may be received in the grooves 264 such that movement of the syringe barrel corresponding to rolling of the syringe may be restricted when disposed on the support platform 256 and engaged by a groove 264. In a similar regard, the channels 266 may be adapted to engage a second portion of a medication receptacle. For example, the concave surface profile of the channels 266 may correspond with finger rest of a syringe. Additionally or alternatively, the concave surface profile of the channels 266 may correspond with a plunger end. In this regard, when the barrel of a syringe is disposed in a groove 264, the finger rest and/or plunger end of the syringe may be engaged by the channel 266 that may restrict motion of the syringe along the length of the groove 264. As such, the syringe may be constrained in at least two degrees of freedom to reduce the potential the syringe mistakenly moves (e.g., slides, is disrupted, or otherwise moved) from the support platform 256. It may also be appreciated that the concave surface profile of the grooves 264 and/or the channels 266 may be operable to retain a cylindrical body (e.g., a vial, bottle, or other cylindrical container) to prevent rolling movement thereof.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

What is claimed is:

1. A system for preparation and management of medical doses, the system comprising:
   a platform base including a scale and a support platform disposed on the platform base;
   a housing configured to house at least one device, wherein the at least one device includes an imaging device;
   a support arm engaged with the housing and the platform base adapted for movement between a first position and a second position;
   a memory;
   a processor in operative communication with the memory, the processor configured to:
      receive digital image data from the imaging device, wherein the digital image data includes data of at least one image associated with the preparation of a medical dose order, wherein the at least one image includes an image of a medication receptacle supportably disposed for weighing,
      receive weight data from the scale, wherein the weight data is associated with the image data and associated with the preparation of the medical dose order,
      associatively store the digital image data and the weight data in the memory, and
      provide an indication of a deviation associated the medical dose order; and
   a display in operative communication with the processor, wherein the display is configured to display the at least one image.

2. The system of claim 1, wherein the system is configured to perform a gravimetric analysis based on the weight data.

3. The system of claim 1, wherein the weight data is appended to dose order metadata.

4. The system of claim 3, wherein the dose order metadata includes data obtained by the imaging device.

5. The system of claim 1, wherein the digital image data and the weight data are captured simultaneously.

6. The system of claim 1, wherein the deviation is a deviation from an anticipated value of a property of the medication receptacle associated with the medical dose order.

7. The system of claim 6, wherein the indication is an alarm, the property is an actual weight, and the anticipated value is an anticipated weight.

8. The system of claim 1, wherein the display is configured to display a work flow corresponding to the preparation of the dose order.

9. The system of claim 1, wherein the digital image data comprises data associated with a portion of a preparation surface and the medication receptacle used in preparation of the medical dose order.

10. A system for preparation and management of medical doses, the system comprising:
- a platform base including a scale and a support platform disposed on the platform base, the support platform configured for disposition of an item thereon;
- a support arm comprising a first portion movably attached to a second portion, the first portion extending above the support platform;
- a housing is connected to the support arm such that at least a portion of the housing extends over the platform base, wherein
  - the housing has a length and width and a curved outer surface that forms an enclosed volume,
  - the housing configured to house at least one device within the enclosed volume, and
  - the at least one device includes an imaging device; and
- a scanning module configured to obtain scanned data from the item disposed on the support platform.

11. The system of claim 10, wherein the scanning module is configured to acquire a barcode scan of the item and generate the scanned data.

12. The system of claim 10, further comprising a shield, wherein the shield and the housing collectively form the enclosed volume.

13. The system of claim 12, wherein the imaging device is disposed within the enclosed volume.

14. The system of claim 10, wherein the curved outer surface includes at least a curved front portion and a curved top portion.

15. The system of claim 10, wherein the housing is supported by the support arm such that the housing is positioned above the scale.

16. A system for preparation of a medical dose, the system comprising:
- a processor;
- a display for providing a work flow corresponding to the preparation of a dose order;
- a platform base including a scale in communication with the processor; and
- a housing configured to house at least one device, wherein
  - the at least one device includes an imaging device,
  - the housing is connected to a support arm comprising at least one portion connected to the platform base,
  - the support arm is adapted for movement between a first position and a second position,
  - the imaging device is in operative communication with the processor, and
  - the imaging device has a depth of field adapted to capture at least a portion of a support platform disposed on the platform base.

17. The system of claim 16, wherein the support platform is configured to supportably receive a medication receptacle, and wherein the imaging device is configured to capture at least one image of the medication receptacle.

18. The system of claim 16, wherein the support platform has one or more medication receptacle engagement feature.

19. The system of claim 18, wherein the one or more medication receptacle engagement feature includes at least one groove.

20. The system of claim 19, wherein the one or more medication receptacle engagement feature includes at least one channel.

* * * * *